(12) United States Patent
Park

(10) Patent No.: US 11,766,236 B2
(45) Date of Patent: Sep. 26, 2023

(54) METHOD AND APPARATUS FOR DISPLAYING ULTRASOUND IMAGE PROVIDING ORIENTATION OF FETUS AND COMPUTER PROGRAM PRODUCT

(71) Applicant: SAMSUNG MEDISON CO., LTD., Hongcheon-gun (KR)

(72) Inventor: Sungwook Park, Seongnam-si (KR)

(73) Assignee: SAMSUNG MEDISON CO., LTD., Hongcheon-gu (KR)

( * ) Notice: Subject to any disclaimer, the term of this patent is extended or adjusted under 35 U.S.C. 154(b) by 170 days.

(21) Appl. No.: 16/670,037

(22) Filed: Oct. 31, 2019

(65) Prior Publication Data
US 2020/0261053 A1 Aug. 20, 2020

(30) Foreign Application Priority Data
Feb. 15, 2019 (KR) .................. 10-2019-0018145

(51) Int. Cl.
*A61B 8/08* (2006.01)
*A61B 8/00* (2006.01)

(52) U.S. Cl.
CPC ............ *A61B 8/0866* (2013.01); *A61B 8/463* (2013.01); *A61B 8/465* (2013.01); *A61B 8/466* (2013.01); *A61B 8/467* (2013.01); *A61B 8/5223* (2013.01); *A61B 8/54* (2013.01)

(58) Field of Classification Search
CPC ......... A61B 8/54; A61B 8/5223; A61B 8/467; A61B 8/466; A61B 8/465; A61B 8/463; A61B 8/0866; A61B 5/684; A61B 8/42; A61B 8/4245; A61B 8/4254
See application file for complete search history.

(56) References Cited

U.S. PATENT DOCUMENTS 6,375,616 B1 * 4/2002 Soferman ............ A61B 8/0866
128/916
8,083,678 B2 12/2011 Abuhamad
(Continued)

FOREIGN PATENT DOCUMENTS

CN 108030515 A 5/2018
EP 3 435 324 A1 1/2019
(Continued)

OTHER PUBLICATIONS

KR-20120056920-A (Year: 2012).*
(Continued)

*Primary Examiner* — Joel Lamprecht
*Assistant Examiner* — Nyrobi Celestine
(74) *Attorney, Agent, or Firm* — Sughrue Mion, PLLC

(57) ABSTRACT

A method of displaying an ultrasound image includes determining a direction of a fetus's head based on a first ultrasound image obtained by scanning a pregnant woman's body in a first direction; determining a direction of a fetus's spine based on a second ultrasound image obtained by scanning the pregnant woman's body in a second direction; determining an orientation of the fetus within the pregnant woman's body based on the directions of the fetus's head and the fetus's spine; and displaying an image representing the orientation of the fetus, together with an ultrasound image obtained by scanning the pregnant woman's body.

17 Claims, 35 Drawing Sheets

(56) References Cited

U.S. PATENT DOCUMENTS

| | | | |
|---|---|---|---|
| 8,882,671 B2* | 11/2014 | Sasaki | G01S 7/52085 600/437 |
| 9,603,579 B2* | 3/2017 | Lee | A61B 8/0866 |
| 9,636,081 B2 | 5/2017 | Reuter et al. | |
| 9,675,320 B2 | 6/2017 | Nakata et al. | |
| 9,734,626 B2 | 8/2017 | Jago et al. | |
| 10,368,833 B2 | 8/2019 | Patruno et al. | |
| 10,368,841 B2 | 8/2019 | Fujiwara et al. | |
| 2005/0251036 A1* | 11/2005 | Abuhamad | A61B 8/0866 600/443 |
| 2007/0287915 A1* | 12/2007 | Akaki | A61B 8/00 600/443 |
| 2011/0282202 A1* | 11/2011 | Lee | G01S 7/52074 600/443 |
| 2013/0177223 A1* | 7/2013 | Lee | G06T 7/0012 382/128 |
| 2014/0296711 A1 | 10/2014 | Lee | |
| 2016/0000401 A1* | 1/2016 | Mienkina | A61B 8/5223 600/443 |
| 2016/0007972 A1* | 1/2016 | Nishiura | A61B 8/5269 600/437 |
| 2016/0015364 A1* | 1/2016 | Kurita | A61B 6/468 600/422 |
| 2016/0081659 A1* | 3/2016 | Perrey | A61B 8/463 600/449 |
| 2017/0000453 A1 | 1/2017 | Feltovich et al. | |
| 2018/0161010 A1* | 6/2018 | Choi | A61B 8/5215 |
| 2019/0209122 A1* | 7/2019 | Jang | A61B 8/4405 |

FOREIGN PATENT DOCUMENTS

| | | |
|---|---|---|
| JP | 2013-215561 A | 10/2013 |
| JP | 2015-171476 A | 10/2015 |
| JP | 2018-068687 A | 5/2018 |
| KR | 20120056920 A * | 6/2012 |
| KR | 10-1495528 B1 | 3/2015 |
| KR | 10-2017-0053685 A | 5/2017 |

OTHER PUBLICATIONS

Y. Zhang et al, "Prenatal diagnosis of fetal unilateral lung agenesis complicated with cardiac malposition", BMC Pregnancy and Childbirth, vol. 13, No. 79, pp. 1-7, Mar. 2013 (Year: 2013).*

Wikipedia "Crown-rump length" Apr. 28, 2019, retrieved from [https://en.wikipedia.org/wiki/Crown-rump_length] (3 pages total).

Wikipedia "Anatomical plane" Sep. 29, 2019, retrieved from [https://en.wikipedia.org/wiki/Anatomical_plane] (4 pages total).

Dupuis, Olivier et al., "Fetal head position during the second stage of labor; Comparison of digital vaginal examination and transabdominal ultrasonographic examination", European Journal of Obstetrics & Gynecology and Reproductive Biology, Elsevier, vol. 123, No. 2, Dec. 1, 2005, pp. 193-197, XP027604485.

Ververs, Ingrid A.P., "Prenatal head position from 12-38 weeks. II. The effects of fetal orientation and placental localization", Early Human Development, Elsevier, vol. 39, No. 2, Oct. 28, 1994, pp. 93-100, XP023126049.

Murphy, Deirdre J. et al., "Study Protocol. IDUS—Instrumental delivery & ultrasound. A multi-centre randomised controlled trial of ultrasound assessment of the fetal head position versus standard care as an approach to prevent morbidity at instrumental delivery", BMC Pregnancy & Childbirth, BioMed Central, vol. 12, No. 1, Sep. 13, 2012, XP021120415. (11 pages total).

Communication dated May 26, 2020 by the European Patent Office in counterpart European Patent Application No. 19210140.0.

* cited by examiner

| | | HEAD DIRECTION | |
| --- | --- | --- | --- |
| | | vertex | breech |
| SPINE DIRECTION |  |  1511 |  1512 } 1505 |
| |  | 1513 | 1514 } 1506 |
| |  | 1515 | 1516 } 1507 |
| |  | 1517 | 1518 } 1508 |
| | | 1501 | 1503 |

METHOD AND APPARATUS FOR DISPLAYING ULTRASOUND IMAGE PROVIDING ORIENTATION OF FETUS AND COMPUTER PROGRAM PRODUCT

CROSS-REFERENCE TO RELATED APPLICATION(S)

This application is based on and claims priority under 35 U.S.C. § 119 to Korean Patent Application No. 10-2019-0018145, filed on Feb. 15, 2019, in the Korean Intellectual Property Office, the disclosure of which is incorporated by reference herein in its entirety.

BACKGROUND

1. Field

The disclosure relates to methods and apparatuses for displaying an ultrasound image and computer program products, and more particularly, to methods of generating and displaying an image representing an orientation of a fetus within a pregnant woman's body.

2. Description of Related Art

Due to their non-invasive and non-destructive characteristics, ultrasound systems have become widely used in medical fields to acquire information about the inside of an object. The ultrasound systems also play a critical role in medical diagnosis because they can provide medical doctors with high-resolution images of an inner area of an object in real-time without the need for performing a surgical procedure to directly incise the object for observation.

An ultrasound system transmits ultrasound signals to an object, receives ultrasound signals (i.e., ultrasound echo signals) reflected from the object, and generates a two- or three-dimensional (2D or 3D) ultrasound image based on the received ultrasound echo signals.

The risk of cardiac malformations in a fetus may be determined based on a position of a fetal heart. For example, when a fetus's heart is normally positioned, the risk of cardiac malformations in the fetus is about 1%. On the other hand, when the fetus's heart is located on the right side of the chest, i.e., the fetus has dextrocardia, the risk of cardiac malformations has been reported to be about 95% or higher. Thus, it is important to accurately determine a position of the fetus's heart to predict the risk of cardiac malformations. However, because the fetus is able to move freely in the womb, even an experienced user may have difficulties in accurately recognizing an orientation of the fetus from an ultrasound cross-sectional image. Thus, an error may occur when predicting the risk of cardiac malformations based on a position of the heart.

SUMMARY

Provided are methods and apparatuses for displaying an image representing an orientation of a fetus within a pregnant woman's body together with an ultrasound image to accurately determine a position of an internal organ of the fetus.

Additional aspects will be set forth in part in the description which follows and, in part, will be apparent from the description, or may be learned by practice of the presented embodiments.

In accordance with an aspect of the disclosure, a method of displaying an ultrasound image includes: determining a direction of a fetus's head based on a first ultrasound image obtained by scanning a pregnant woman's body in a first direction; determining a direction of a fetus's spine based on a second ultrasound image obtained by scanning the pregnant woman's body in a second direction; determining an orientation of the fetus within the pregnant woman's body based on the directions of the fetus's head and the fetus's spine; and displaying an image representing the orientation of the fetus, together with an ultrasound image obtained by scanning the pregnant woman's body.

In accordance with another aspect of the disclosure, an apparatus for displaying an ultrasound image includes: at least one processor configured to determine a direction of a fetus's head based on a first ultrasound image obtained by scanning a pregnant woman's body in a first direction, determine a direction of a fetus's spine based on a second ultrasound image obtained by scanning the pregnant woman's body in a second direction, and determine an orientation of the fetus within the pregnant woman's body based on the directions of the fetus's head and the fetus's spine; and a display displaying an image representing the orientation of the fetus, together with an ultrasound image obtained by scanning the pregnant woman's body.

In accordance with another aspect of the disclosure, a computer program product includes at least one computer-readable recording medium having stored therein a program for performing the method of displaying an ultrasound image.

BRIEF DESCRIPTION OF THE DRAWINGS

The above and other aspects, features, and advantages of certain embodiments of the disclosure will be more apparent from the following description taken in conjunction with the accompanying drawings, in which.

DETAILED DESCRIPTION

Figure 1:
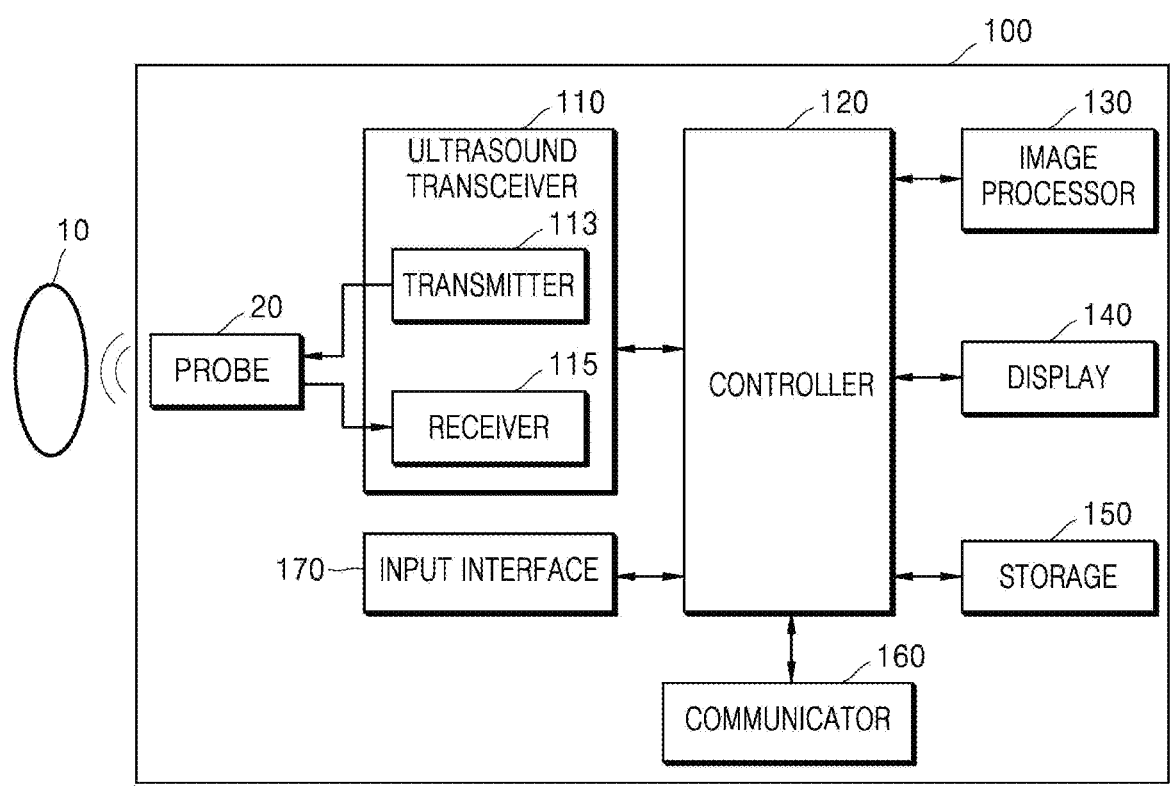
FIG. 1 is a block diagram of a configuration of an ultrasound diagnosis apparatus according to an embodiment.

Certain embodiments are described in greater detail below with reference to the accompanying drawings.

In the following description, the same drawing reference numerals are used for the same elements even in different drawings. The matters defined in the description, such as detailed construction and elements, are provided to assist in a comprehensive understanding of exemplary embodiments. Thus, it is apparent that exemplary embodiments can be carried out without those specifically defined matters. Also, well-known functions or constructions are not described in detail since they would obscure exemplary embodiments with unnecessary detail.

Terms such as "part" and "portion" used herein denote those that may be embodied by software or hardware. According to exemplary embodiments, a plurality of parts or portions may be embodied by a single unit or element, or a single part or portion may include a plurality of elements. Expressions such as "at least one of," when preceding a list of elements, modify the entire list of elements and do not modify the individual elements of the list.

In the embodiments of the disclosure, an image may include any medical image acquired by various medical imaging apparatuses such as a magnetic resonance imaging (MRI) apparatus, a computed tomography (CT) apparatus, an ultrasound imaging apparatus, or an X-ray apparatus.

Also, in the present specification, an "object", which is a thing to be imaged, may include a human, an animal, or a part thereof. For example, an object may include a part of a human, that is, an organ or a tissue, or a phantom. While descriptions are provided below with respect to an example in which an image captured of a pregnant woman's body and a fetus therein as an object is displayed, the disclosure may be applied to display captured images of various objects.

Throughout the specification, an ultrasound image refers to an image of an object processed based on ultrasound signals transmitted to the object and reflected therefrom. An ultrasound image may be a two- or three-dimensional (2D or 3D) image.

FIG. 1 is a block diagram illustrating a configuration of an ultrasound diagnosis apparatus 100, i.e., a diagnostic apparatus, according to an embodiment of the disclosure.

Referring to FIG. 1, the ultrasound diagnosis apparatus 100 may include a probe 20, an ultrasound transceiver 110, a controller 120, an image processor 130, one or more displays 140, a storage 150, e.g., a memory, a communicator 160, i.e., a communication device or an interface, and an input interface 170.

The ultrasound diagnosis apparatus 100 may be of a cart-type or a portable-type ultrasound diagnosis apparatus, which is portable, moveable, mobile, or hand-held. Examples of the portable-type ultrasound diagnosis apparatus may include a smart phone, a laptop computer, a personal digital assistant (PDA), and a tablet personal computer (PC), each of which may include a probe and a software application, but embodiments are not limited thereto.

The probe 20 may include a plurality of transducers. The plurality of transducers may transmit ultrasound signals to an object 10 in response to transmitting signals received by the probe 20, from a transmitter 113. The plurality of transducers may receive ultrasound signals reflected from the object 10 to generate reception signals. In addition, the probe 20 and the ultrasound diagnosis apparatus 100 may be formed in one body (e.g., disposed in a single housing), or the probe 20 and the ultrasound diagnosis apparatus 100 may be formed separately (e.g., disposed separately in separate housings) but linked wirelessly or via wires. In addition, the ultrasound diagnosis apparatus 100 may include one or more probes 20 according to embodiments.

The controller 120 may control the transmitter 113 for the transmitter 113 to generate transmitting signals to be applied to each of the plurality of transducers based on a position and a focal point of the plurality of transducers included in the probe 20.

The controller 120 may control the ultrasound receiver 115 to generate ultrasound data by converting reception signals received from the probe 20 from analogue to digital signals and summing the reception signals converted into digital form, based on a position and a focal point of the plurality of transducers.

The image processor 130 may generate an ultrasound image by using ultrasound data generated from the ultrasound receiver 115.

The display 140 may display a generated ultrasound image and various pieces of information processed by the ultrasound diagnosis apparatus 100. The ultrasound diagnosis apparatus 100 may include two or more displays 140 according to the present exemplary embodiment. The display 140 may include a touch screen in combination with a touch panel.

The controller 120 may control the operations of the ultrasound diagnosis apparatus 100 and flow of signals between the internal elements of the ultrasound diagnosis apparatus 100. The controller 120 may include a memory for storing a program or data to perform functions of the ultrasound diagnosis apparatus 100 and a processor and/or a microprocessor (not shown) for processing the program or data. For example, the controller 120 may control the operation of the ultrasound diagnosis apparatus 100 by receiving a control signal from the input interface 170 or an external apparatus.

The ultrasound diagnosis apparatus 100 may include the communicator 160 and may be connected to external apparatuses, for example, servers, medical apparatuses, and portable devices such as smart phones, tablet personal computers (PCs), wearable devices, etc., via the communicator 160.

The communicator 160 may include at least one element capable of communicating with the external apparatuses. For example, the communicator 160 may include at least one among a short-range communication module, a wired communication module, and a wireless communication module.

The communicator 160 may receive a control signal and data from an external apparatus and transmit the received control signal to the controller 120 so that the controller 120 may control the ultrasound diagnosis apparatus 100 in response to the received control signal.

The controller 120 may transmit a control signal to the external apparatus via the communicator 160 so that the external apparatus may be controlled in response to the control signal of the controller 120.

For example, the external apparatus connected to the ultrasound diagnosis apparatus 100 may process the data of the external apparatus in response to the control signal of the controller 120 received via the communicator 160.

A program for controlling the ultrasound diagnosis apparatus 100 may be installed in the external apparatus. The program may include command languages to perform part of operation of the controller 120 or the entire operation of the controller 120.

The program may be pre-installed in the external apparatus or may be installed by a user of the external apparatus by downloading the program from a server that provides applications. The server that provides applications may include a recording medium where the program is stored.

The storage 150 may store various data or programs for driving and controlling the ultrasound diagnosis apparatus 100, input and/or output ultrasound data, ultrasound images, applications, etc.

The input interface 170 may receive a user's input to control the ultrasound diagnosis apparatus 100 and may include a keyboard, button, keypad, mouse, trackball, jog switch, knob, a touchpad, a touch screen, a microphone, a motion input means, a biometrics input means, etc. For example, the user's input may include inputs for manipulating buttons, keypads, mice, trackballs, jog switches, or knobs, inputs for touching a touchpad or a touch screen, a voice input, a motion input, and a bioinformation input, for example, iris recognition or fingerprint recognition, but an exemplary embodiment is not limited thereto.

An example of the ultrasound diagnosis apparatus 100 according to the present exemplary embodiment is described below with reference to FIG. 2.

Figure 2:
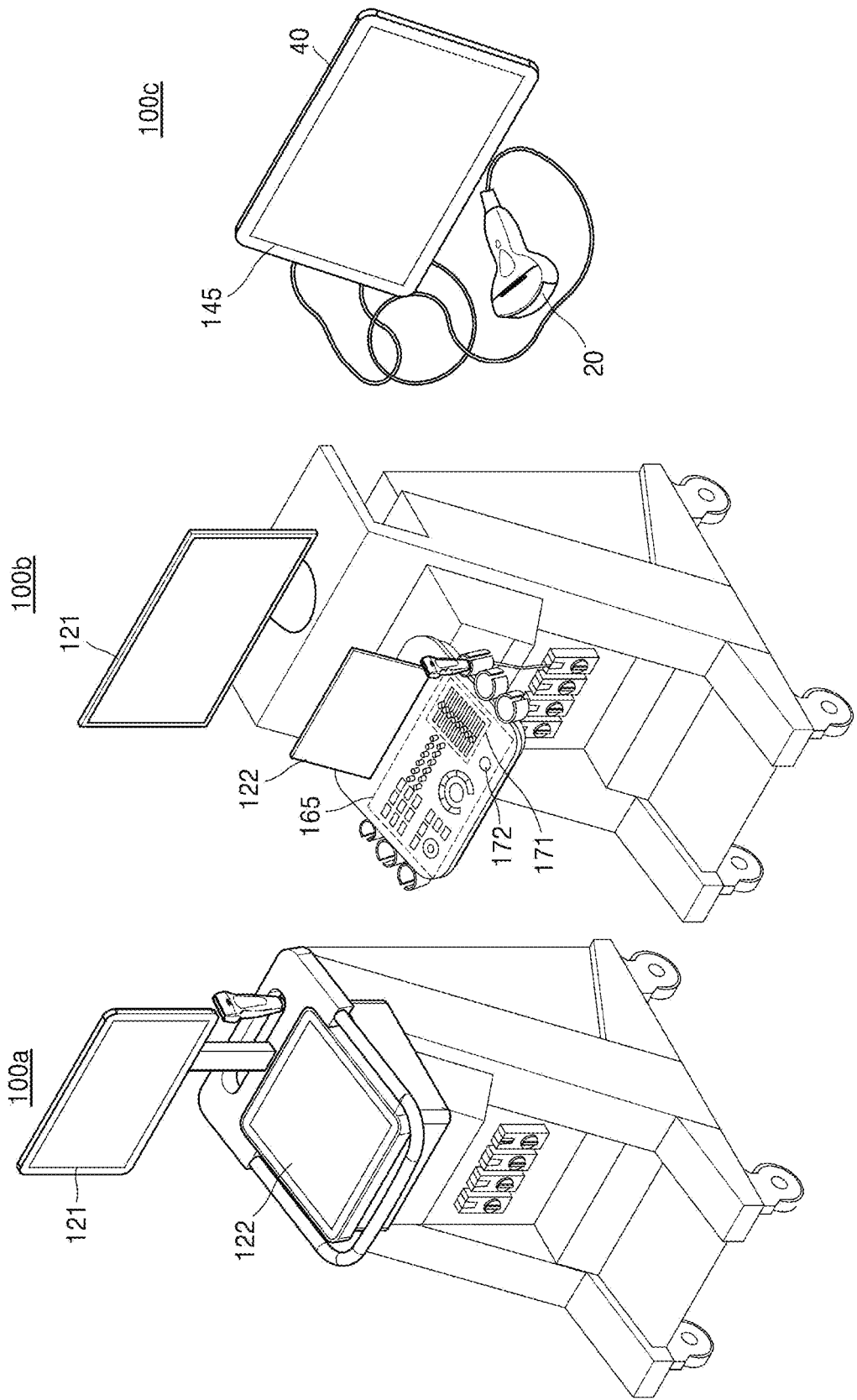
FIG. 2 illustrates examples of ultrasound diagnosis apparatuses according to an embodiment.

FIG. 2 illustrates examples of the ultrasound diagnosis apparatus 100a, 100b, and 100c according to the present exemplary embodiment.

Referring to FIG. 2, the ultrasound diagnosis apparatus 100a may include a main display 121 and a sub-display 122. At least one among the main display 121 and the sub-display 122 may include a touch screen. The main display 121 and the sub-display 122 may display ultrasound images and/or various information processed by the ultrasound diagnosis apparatus 100a. The main display 121 and the sub-display 122 may provide graphical user interfaces (GUI), thereby receiving user's inputs of data to control the ultrasound diagnosis apparatus 100a. For example, the main display 121 may display an ultrasound image and the sub-display 122 may display a control panel to control display of the ultrasound image as a GUI. The sub-display 122 may receive an input of data to control the display of an image through the control panel displayed as a GUI. The ultrasound diagnosis apparatus 100a may control the display of the ultrasound image on the main display 121 by using the input control data.

Referring to FIG. 2, the ultrasound diagnosis apparatus 100b may include a control panel 165. The control panel 165 may include buttons, trackballs, jog switches, or knobs, and may receive data to control the ultrasound diagnosis apparatus 100b from the user. For example, the control panel 165 may include a time gain compensation (TGC) button 171 and a freeze button 172. The TGC button 171 is to set a TGC value for each depth of an ultrasound image. Also, when an input of the freeze button 172 is detected during scanning an ultrasound image, the ultrasound diagnosis apparatus 100b may keep displaying a frame image at that time point.

The buttons, trackballs, jog switches, and knobs included in the control panel 165 may be provided as a GUI to the main display 121 or the sub-display 122.

Referring to FIG. 2, the ultrasound diagnosis apparatus 100c may include a portable device. An example of the portable ultrasound diagnosis apparatus may include, for example, smart phones including probes and applications, laptop computers, personal digital assistants (PDAs), or tablet PCs, but an exemplary embodiment is not limited thereto.

The ultrasound diagnosis apparatus 100c may include the probe 20 and a main body 40. The probe 20 may be connected to one side of the main body 40 by wire or wirelessly. The main body 40 may include a touch screen 145. The touch screen 145 may display an ultrasound image, various pieces of information processed by the ultrasound diagnosis apparatus 100c, and a GUI.

Figure 3A:
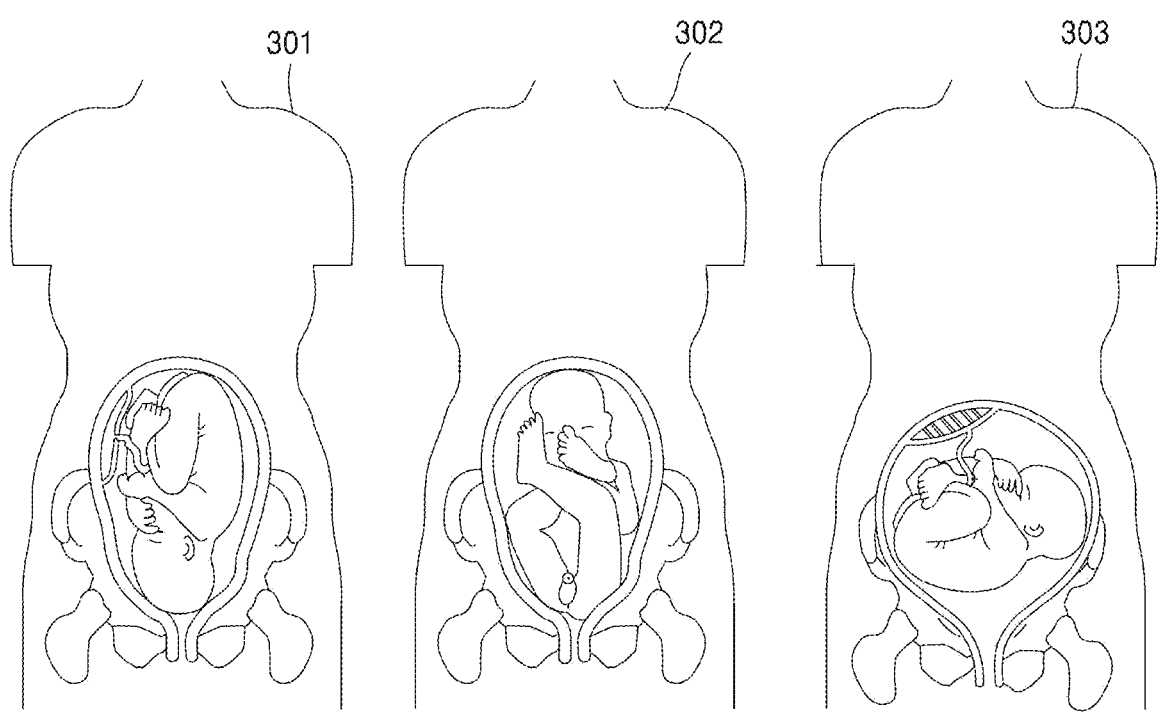
FIGS. 3A and 3B are diagrams for explaining a general method of diagnosing a fetus by using an ultrasound diagnosis apparatus.
Figure 3B:
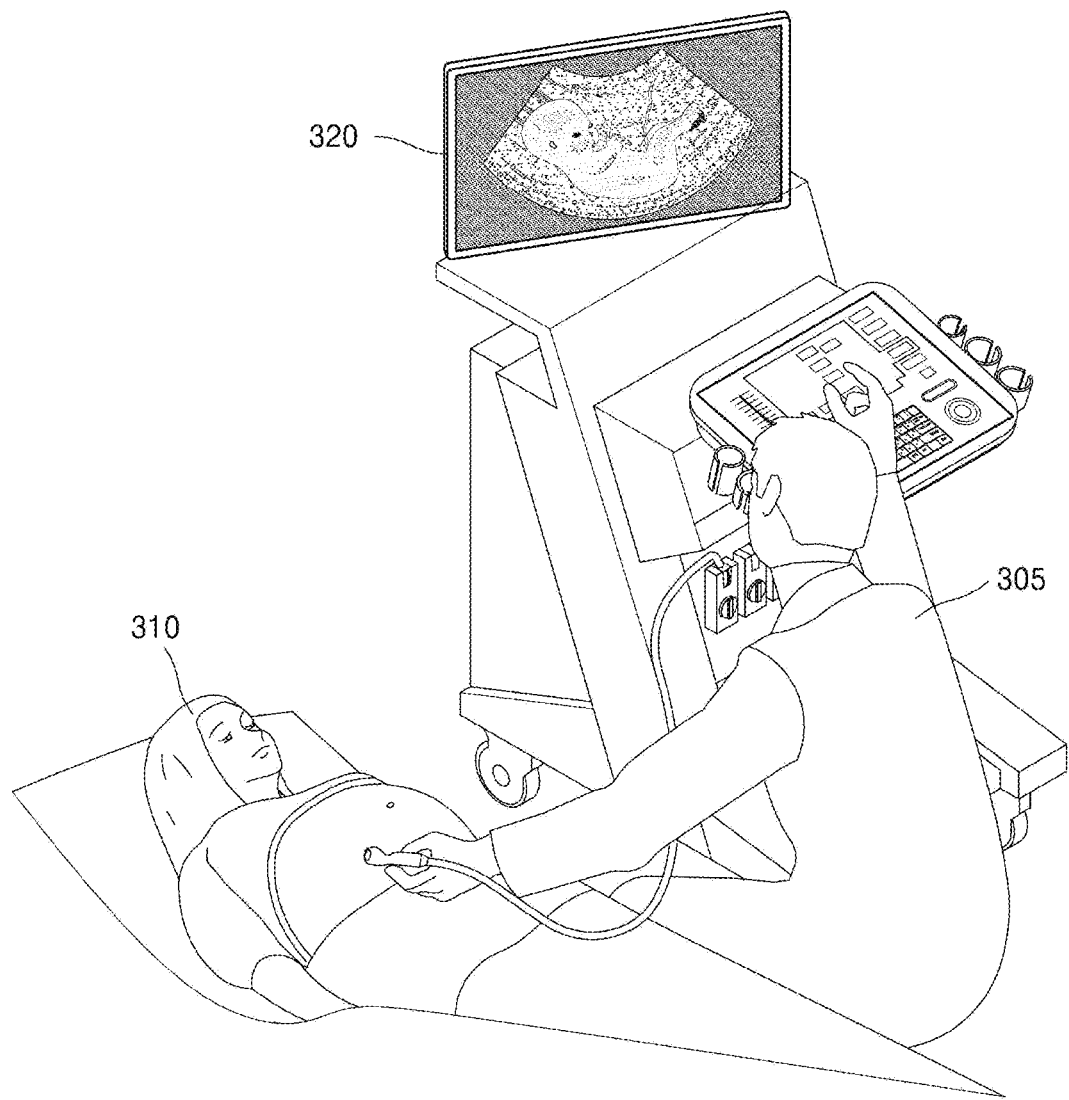

FIGS. 3A and 3B are diagrams for explaining a method of diagnosing a fetus by using an ultrasound diagnosis apparatus according to an embodiment.

FIG. 3A illustrates a direction in which a fetus is positioned within a pregnant woman's body. Images 301 through 303 shown in FIG. 3A respectively represent a longitudinal lie vertex presentation, a longitudinal lie breech presentation, and a transverse lie shoulder presentation.

FIG. 3B illustrates an example in which a user 305 diagnoses a fetus within a pregnant woman's body 310 by using an ultrasound diagnosis apparatus 320. When the user 505 diagnoses the fetus by using the ultrasound diagnosis apparatus 320, information about left and right sides of the fetus is important in determining whether organs of the fetus are in a normal position (situs solitus) or abnormal position (situs inversus). However, because the fetus may be positioned within a pregnant woman's body in various directions as shown in FIG. 3A, information about left and right sides of the pregnant woman's body may be different from the information about the left and right sides of the fetus, which makes it difficult to identify the left and right sides of the fetus.

To determine information about the left and right sides of the fetus, according to a method of the related art, the user 305 checks information related to an position of the fetus (e.g. information related to whether the fetus is in a vertex presentation or breech presentation) and directly determines the left and right sides thereof.

However, the user may have difficulties in intuitively determining the left and right sides of the fetus only based on a cross-section of the fetus. Thus, according to various embodiments of the disclosure, there are provided a method and apparatus for displaying an image representing an orientation of a fetus within a pregnant woman's body together with an ultrasound image such that a user may accurately and intuitively diagnose the fetus.

Figure 4A:
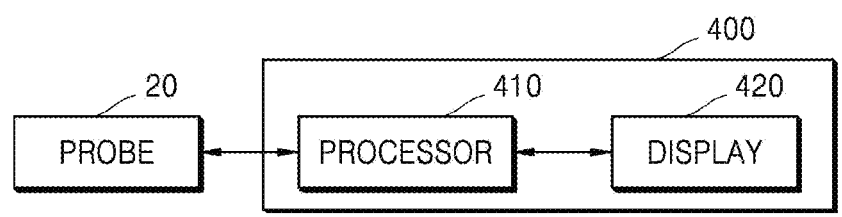
FIGS. 4A and 4B are block diagrams of configurations of an ultrasound image display apparatus, according to an embodiment.
Figure 4B:
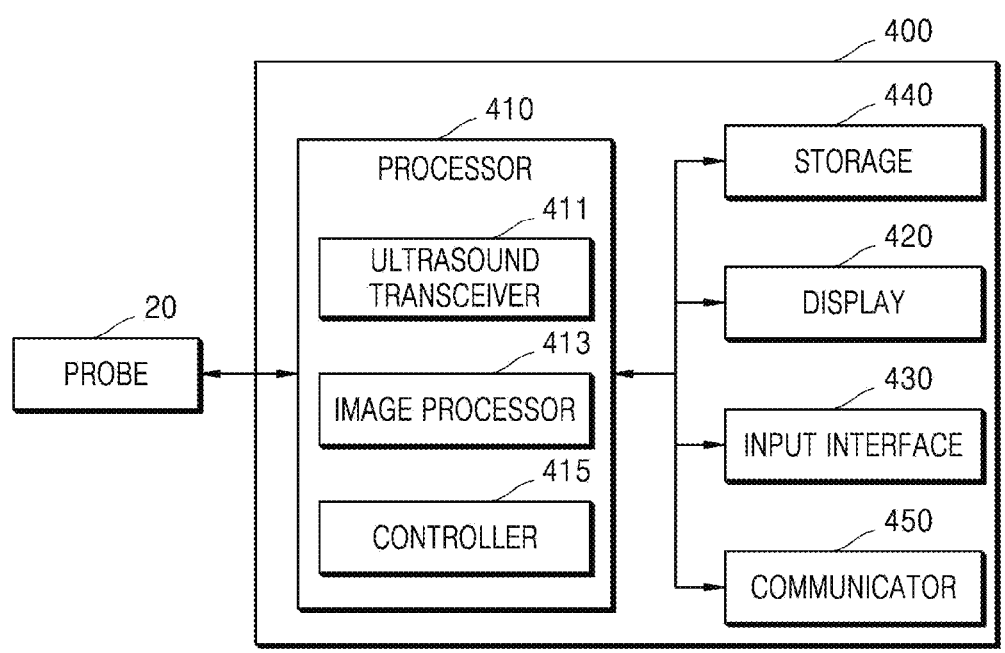

FIGS. 4A and 4B are block diagrams of configurations of an ultrasound image display apparatus 400, according to an embodiment.

The ultrasound image display apparatus 400 of FIGS. 4A and 4B is an apparatus for displaying an ultrasound image. The ultrasound image display apparatus 400 may be included in or include the ultrasound diagnosis apparatus 100 of FIG. 1. Alternatively, the ultrasound image display apparatus 400 may be a separate electronic device connected to the ultrasound diagnosis apparatus 100 and display an ultrasound image obtained from the ultrasound diagnosis apparatus 100 or an external device.

Descriptions of the ultrasound diagnosis apparatus 100 of FIG. 1 may be applied to the components of the ultrasound image display apparatus 400 of FIGS. 4A and 4B, and thus, will not be repeated below.

Referring to FIG. 4A, according to an embodiment, the ultrasound image display apparatus 400 may include a processor 410 and a display 420. However, the ultrasound image display apparatus 400 may include more components than those shown in FIG. 4A. For example, according to an embodiment, the ultrasound image display apparatus 400 may further include at least one of an input interface 430, a storage 440, and a communicator 450, as shown in FIG. 4B.

Furthermore, according to an embodiment, the ultrasound image display apparatus 400 may include or be connected to a probe 20. The ultrasound image display apparatus 400 may display an ultrasound image of an object acquired via the probe 20.

According to an embodiment, an ultrasound transceiver 411, an image processor 413, and a controller 415 of the processor 410 may respectively perform at least some of the operations and functions of the ultrasound transceiver 110, the image processor 130, and the controller 120 described with reference to FIG. 1. According to an embodiment, the display 420, the input interface 430, the storage 440, and the communicator 450 may respectively correspond to the display 140, the input interface 170, the storage 150, and the communicator 160. Descriptions that are already provided above with respect to the corresponding components will be omitted here.

Although FIGS. 4A and 4B show that the ultrasound image display apparatus 400 includes a single processor for convenience, embodiments are not limited thereto, and the ultrasound image display apparatus 400 may include a plurality of processors. When the ultrasound image display apparatus 400 includes the plurality of processors, operations of the processor 410 to be described below may be respectively performed by the processors.

The components of the ultrasound image display apparatus 400 are now described in more detail.

According to an embodiment of the disclosure, the processor 410 of the ultrasound image display apparatus 400 may determine an orientation of a fetus within a pregnant woman's body. The orientation of the fetus may be an orientation of an axis of the fetus relative to the pregnant woman's body. For example, the orientation of the fetus may include information about whether the fetus is longitudinally or transversely positioned with respect to the pregnant woman's body, information about whether a fetus's head or buttocks is facing towards a pregnant woman's cervix, and information about a direction in which an anterior portion of the fetus points towards the pregnant woman's body.

The processor 410 may determine one of directions of a fetus's head and spine based on a first ultrasound image obtained by scanning the pregnant woman's body in a first direction and the other of the directions based on a second ultrasound image obtained by scanning the pregnant woman's body in a second direction.

The first direction may be different from the second direction. The first direction may be perpendicular to the second direction. For example, the first direction may be a direction in which one of longitudinal and transverse planes of the pregnant woman's body is scanned, and the second direction may be a direction in which the other of the longitudinal and transverse planes is scanned. As another example, the first direction may be a direction in which a sagittal plane, a median plane, or an anteroposterior plane of the pregnant woman's body is scanned, and the second direction may be a direction in which an axial plane, a lateral plane, or a horizontal plane of the pregnant woman's body is scanned.

For example, the processor 410 may first determine a direction of the fetus's head based on the first ultrasound image obtained by scanning the pregnant woman's body along the first direction and then a direction of the fetus's spine based on the second ultrasound image obtained by scanning the pregnant woman's body along the second direction. However, embodiments are not limited thereto, and the processor 410 may first determine the direction of the fetus's spine based on the first ultrasound image and then the direction of the fetus's head based on the second ultrasound image.

The processor 410 may determine the orientation of the fetus within the pregnant woman's body based on the directions of the fetus's head and spine.

The display 420 may display an image representing the orientation of the fetus together with an ultrasound image obtained by scanning the pregnant woman's body. The display 420 may display an image representing the orientation of the fetus together with a real-time ultrasound image obtained by scanning the mother['s body, thereby allowing the user to easily identify information about left and right sides of a cross-sectional image of the fetus.

Operations of the components of the ultrasound image display apparatus 400 for displaying an image representing the orientation of the fetus are now described in more detail.

When an object is scanned, the display 420 may display a marker indicating an orientation of the probe 20 for scanning the object to obtain an ultrasound image. The user may scan, based on the marker being displayed on a screen of the display 420, the pregnant woman's body while holding the probe 20 in one hand in a direction corresponding to the marker being displayed. The processor 410 may determine an orientation of the fetus based on a direction of a fetus's head, a direction of a fetus's spine, and an orientation of the probe 20.

Figure 5A:
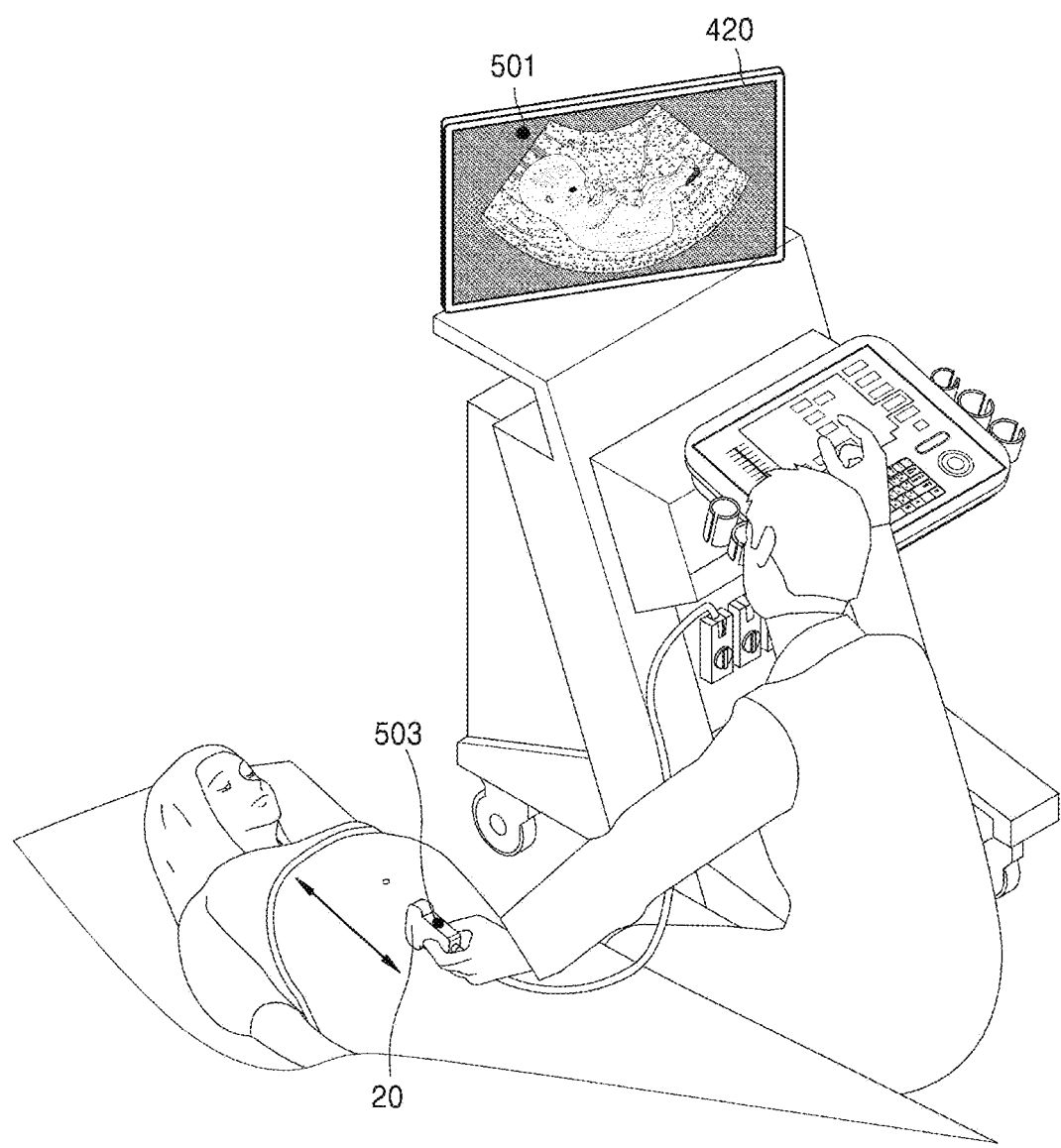
FIGS. 5A through 5C are diagrams for explaining markers used to indicate an orientation of a probe, according to an embodiment.
Figure 5B:
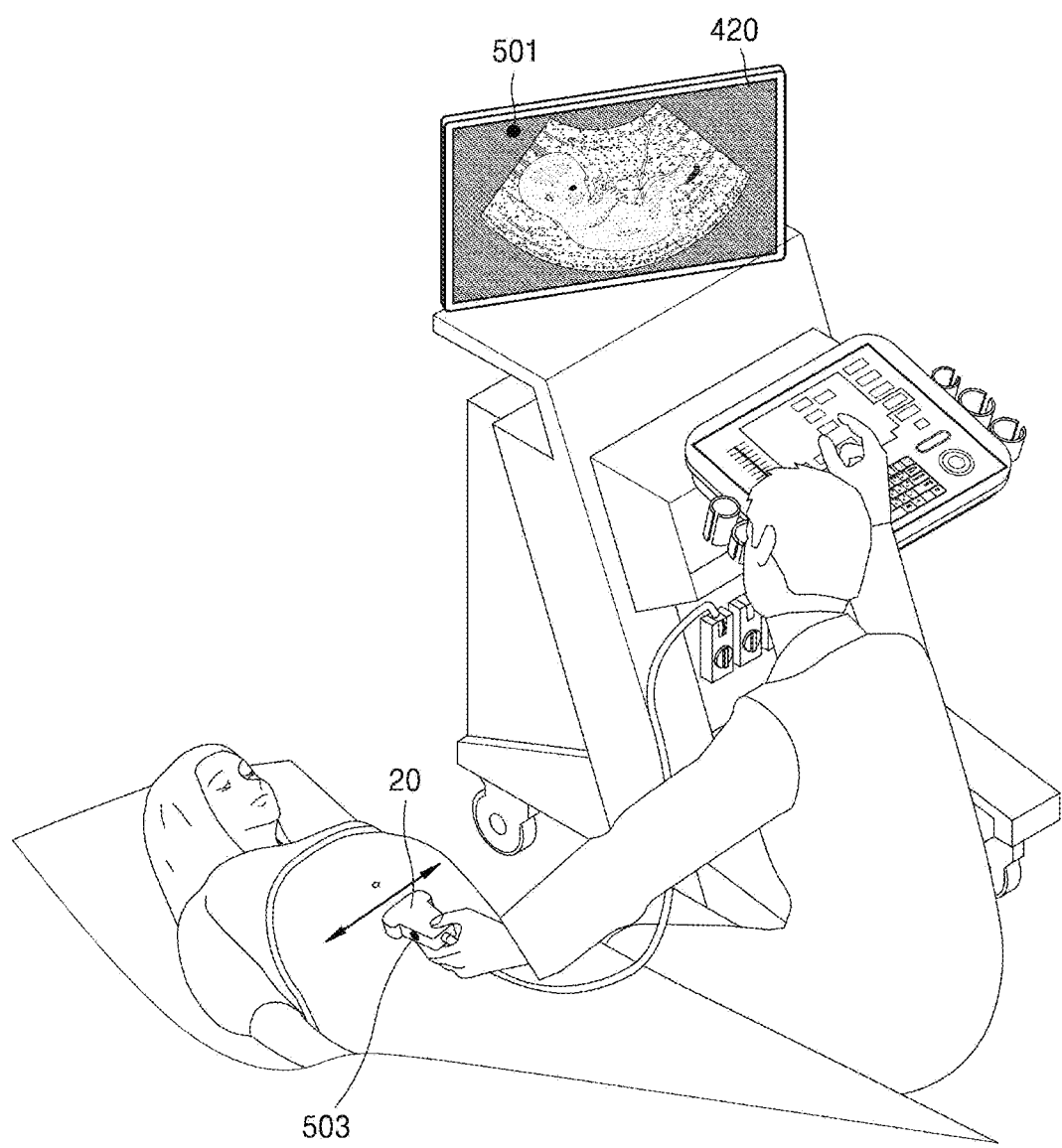
Figure 5C:
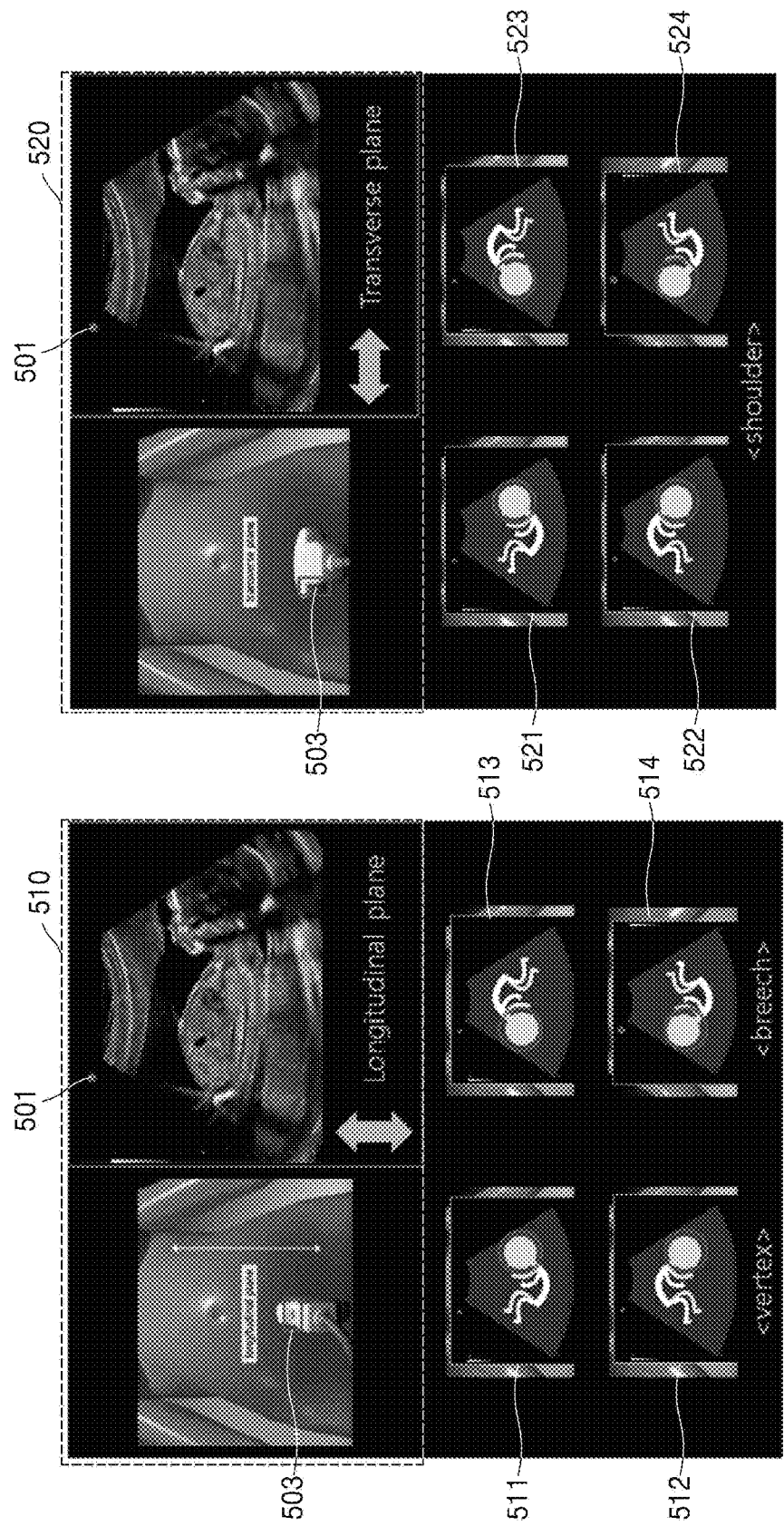

FIGS. 5A through 5C are diagrams for explaining markers used to indicate an orientation of the probe 20, according to an embodiment.

FIG. 5A illustrates an example in which a user keeps the probe 20 in a vertical position and scans a mother's body in a longitudinal direction with the probe 20. By taking into account that a marker 501 is displayed at the top of the screen of the display 420, the user may hold the probe 20 with one hand such that a marker 503 attached to the probe 20 is positioned at the top of the probe 20 and may scan the pregnant woman's body with reference to a marker 501.

FIG. 5B illustrates an example in which the user scans the pregnant woman's body in a transverse plane with the probe 20 in a horizontal position. By taking into account that a marker 501 is displayed on the left side of the screen of the display 420, the user may hold the probe 20 with one hand such that a marker 503 attached to the probe 20 is positioned on the left side of the probe 20 and may scan the pregnant woman's body with reference to the marker 501.

FIG. 5C illustrates a relationship between the marker 503 attached to the probe 20 and the marker 501 displayed on the screen.

FIG. 5C illustrates an example in which the user keeps the probe 20 in a vertical position and scans the pregnant woman's body in a longitudinal plane with the probe 20. By taking into account that the marker 501 is displayed at the top of the screen of the display 420, the user may hold the probe 20 with one hand such that the marker 503 attached to the probe 20 is positioned at the top of the probe 20 and may scan the pregnant woman's body with reference to the marker 501. When a fetus positioned within the pregnant woman's body in a longitudinal direction is scanned as shown in the image 510, the ultrasound image display apparatus 400 may obtain an ultrasound image 511, 512, 513, or 514.

The user or the ultrasound image display apparatus 400 may determine, based on the ultrasound images 511 and 512, that the fetus is positioned within the pregnant woman's body in a longitudinal lie vertex presentation. As shown in the ultrasound images 511 and 512, when a head of the fetus in the ultrasound images 511 and 512 is located on the right side thereof, the user or the ultrasound image display apparatus 400 may determine that the fetus is positioned within the pregnant woman's body in the longitudinal lie vertex presentation.

The user or the ultrasound image display apparatus 400 may determine, based on the ultrasound images 513 and 514, that the fetus is positioned within the pregnant woman's body in a longitudinal lie breech presentation. As shown in the ultrasound images 513 and 514, when the fetus's head in the ultrasound images 513 and 514 is located on the left side thereof, the user or the ultrasound image display apparatus 400 may determine that the fetus is positioned within the pregnant woman's body in the longitudinal lie breech presentation.

An image 520 of FIG. 5C is obtained by scanning the pregnant woman's body in a transverse plane with the probe 20 in a horizontal position. By taking into account that the marker 501 is displayed on the left side of the screen of the display 420, the user may hold the probe 20 with one hand such that the marker 503 attached to the probe 20 is positioned on the left side thereof and may scan the pregnant woman's body with reference to the marker 501. When the fetus positioned within the pregnant woman's body in a transverse direction is scanned as shown in the image 520, the ultrasound image display apparatus 400 may obtain an ultrasound image 521, 522, 523, or 524.

The user or the ultrasound image display apparatus 400 may determine, based on the ultrasound image 521, 522, 523, or 524, that the fetus is positioned within the pregnant woman's body in a transverse lie shoulder presentation. As shown in the ultrasound image 521, 522, 523, or 524, when the fetus's head in an ultrasound image obtained by scanning the pregnant woman's body in a transverse direction is positioned on the right or left side of the ultrasound image, the user or the ultrasound image display apparatus 400 may determine that the fetus is positioned within the pregnant woman's body in the transverse line shoulder presentation.

The ultrasound image display apparatus 400 may display a marker indicating an orientation of the probe 20 to allow the user to continuously scan the pregnant woman's body in a specific direction to obtain an ultrasound image.

According to an embodiment of the disclosure, the ultrasound image display apparatus 400 may respectively obtain first and second ultrasound images by scanning the pregnant woman's body in first and second directions.

Figure 6:
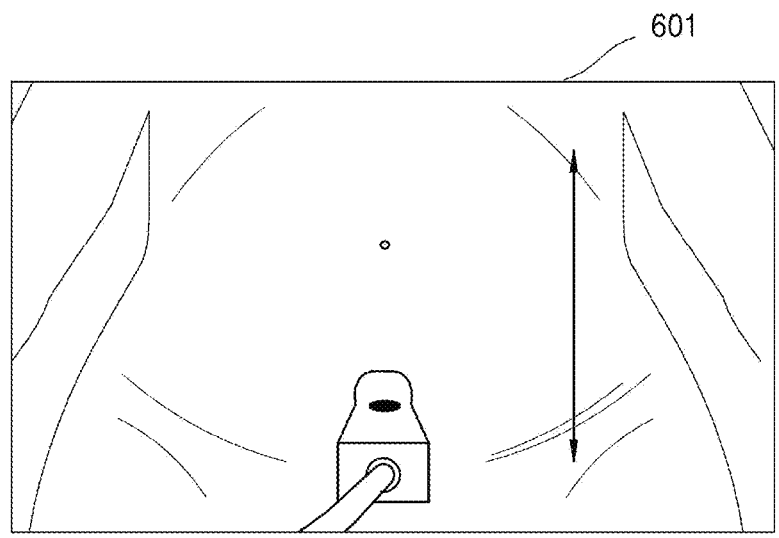
FIG. 6 is a diagram for explaining a direction in which a user scans a pregnant woman's body via a probe, according to an embodiment.
Figure 6:
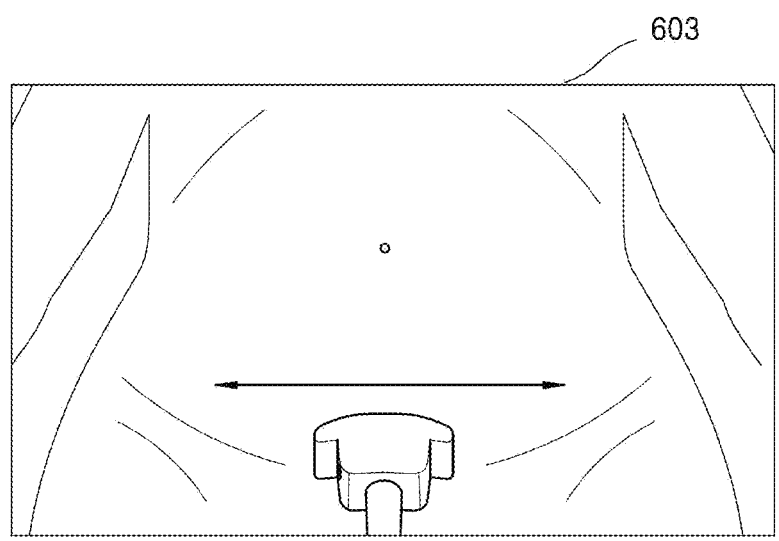

As shown in an image 601 of FIG. 6, the processor 410 may obtain an ultrasound image by scanning a cross-section of a fetus along a longitudinal axis of the pregnant woman's body. The processor 410 may obtain an ultrasound image by scanning the pregnant woman's body in a longitudinal plane. Furthermore, as shown in an image 603 of FIG. 6, the processor 410 may obtain an ultrasound image by scanning a cross-section of the fetus along a transverse axis of the pregnant woman's body. The processor 410 may obtain an ultrasound image by scanning the pregnant woman's body in a transverse plane.

According to an embodiment of the disclosure, the ultrasound image display apparatus 400 may display a UI for guiding a user through a direction in which the object is to be scanned.

The processor 410 may control the display 420 to display a UI for guiding the user to scan the pregnant woman's body in a first direction.

Figure 7:
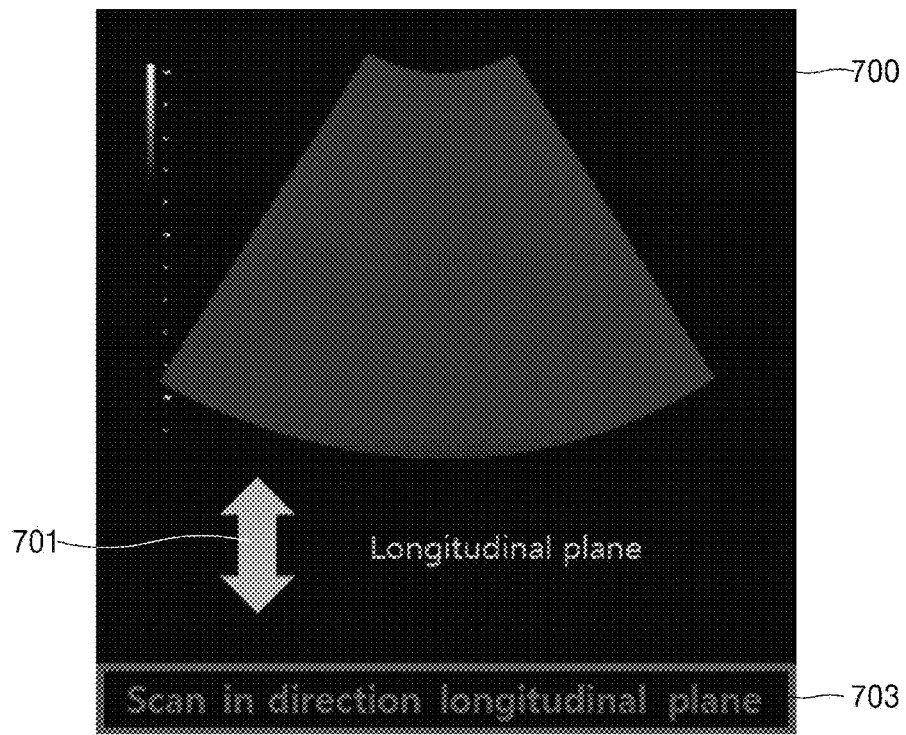
FIG. 7 illustrates a user interface (UI) displayed by an ultrasound image display apparatus, according to an embodiment.

The ultrasound image display apparatus 400 may display a UI for guiding a user through a scanning direction. The scanning direction may be represented by at least one of a letter, an image, and a symbol. For example, referring to FIG. 7, the ultrasound image display apparatus 400 may display an image 700 having at least one of an arrow 701 and a guiding phrase 703 included therein such that the pregnant woman's body is scanned in a longitudinal plane.

According to guidance by the ultrasound image display apparatus 400, the user may manipulate the probe 20 to scan the pregnant woman's body in the longitudinal plane.

FIGS. 8A through 8D illustrate ultrasound images obtained by performing a scan along an orientation of a fetus within a pregnant woman's body.

Figure 8A:
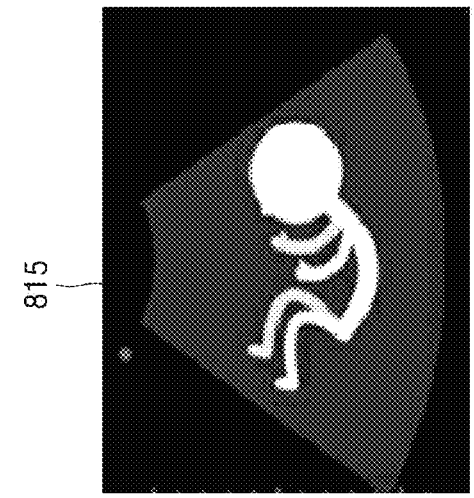
FIGS. 8A through 8D illustrate ultrasound images obtained by performing a scan along an orientation of a fetus within a pregnant woman's body according to an embodiment.
Figure 8A:
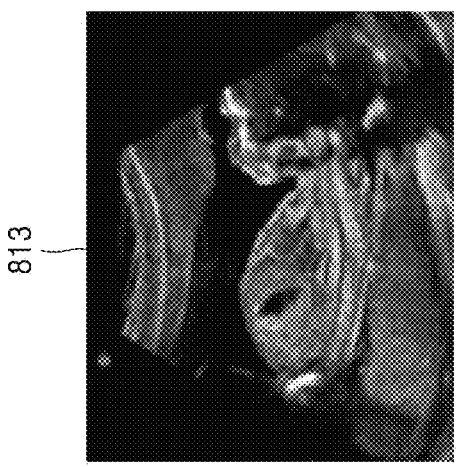
Figure 8A:
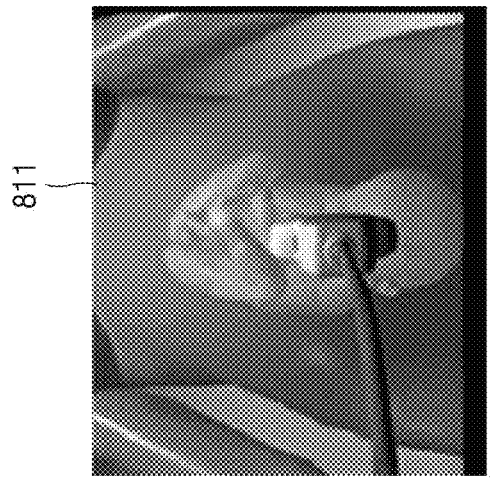

When the fetus is positioned as shown in an image 811 of FIG. 8A, an ultrasound image 813 may be obtained by scanning the pregnant woman's body in a longitudinal direction via the probe 20. The ultrasound image 813 may show a cross-section of the fetus having the same orientation as illustrated in an image 815. A head of the fetus in the ultrasound image 813 may be located right with respect to the torso.

Figure 8B:
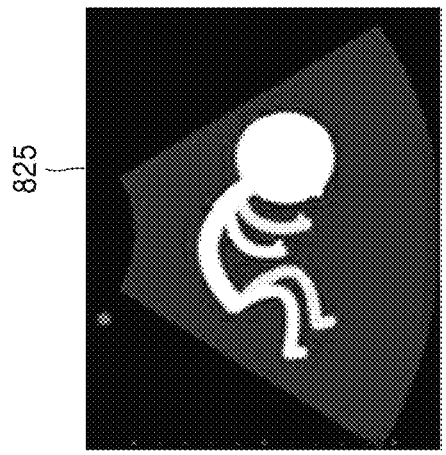
Figure 8B:
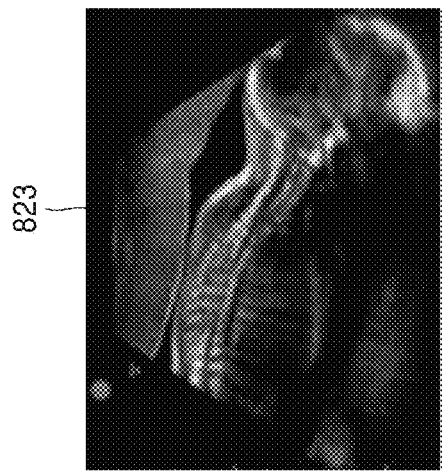
Figure 8B:
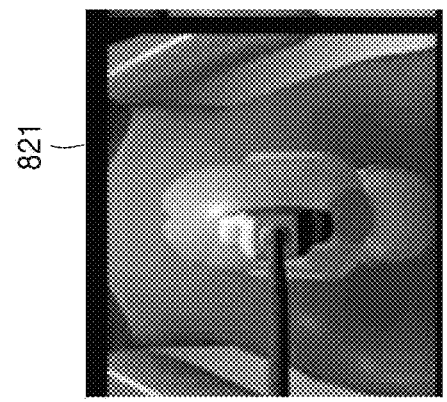

When the fetus is positioned as shown in an image 812 of FIG. 8B, an ultrasound image 823 may be obtained by scanning the pregnant woman's body in the longitudinal direction via the probe 20. The ultrasound image 823 may show a cross-section of the fetus having the same orientation as illustrated in an image 825. The head of the fetus in the ultrasound image 823 may be located with respect to the torso.

Figure 8C:
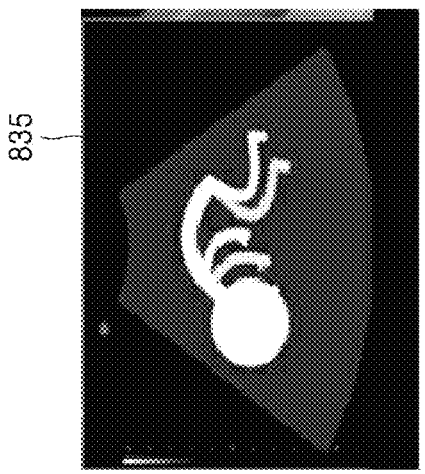
Figure 8C:
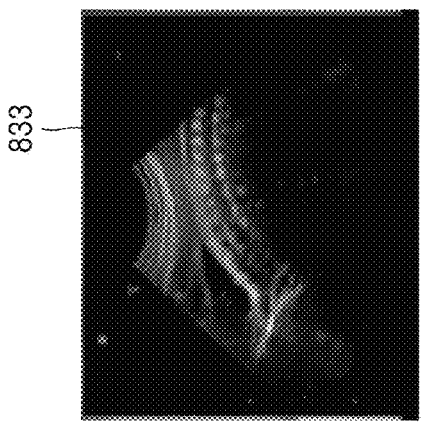
Figure 8C:
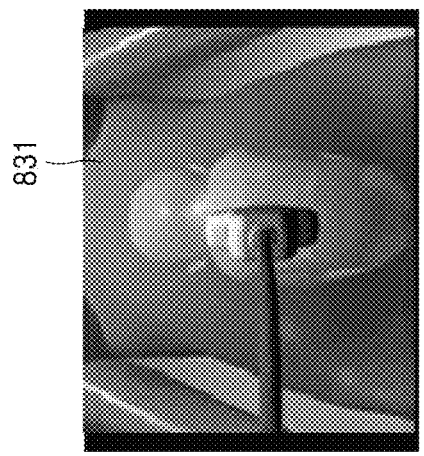

When the fetus is positioned as shown in an image 831 of FIG. 8C, an ultrasound image 833 may be obtained by scanning the pregnant woman's body in the longitudinal direction via the probe 20. The ultrasound image 833 may show a cross-section of the fetus having the same orientation as illustrated in an image 835. The head of the fetus in the ultrasound image 833 may be located left with respect to the torso.

Figure 8D:
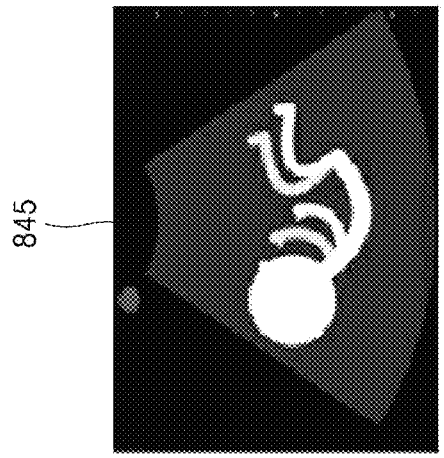
Figure 8D:
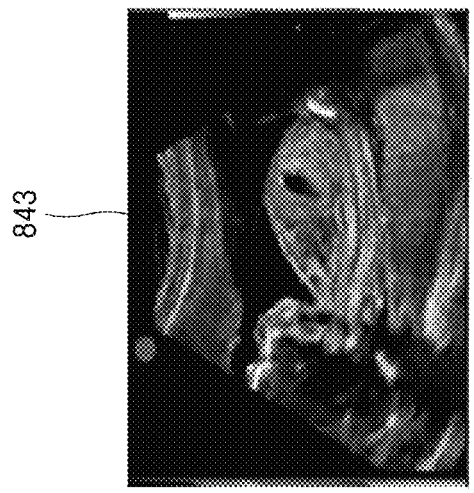
Figure 8D:
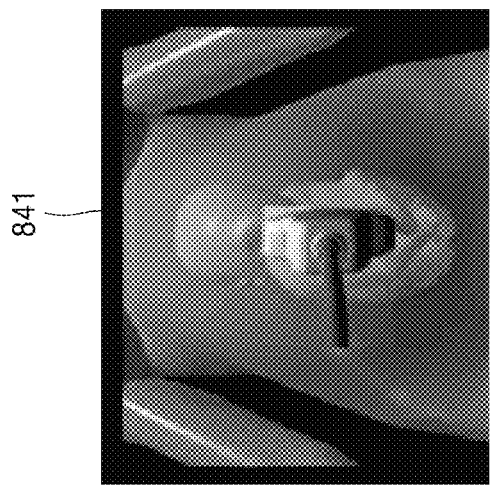

When the fetus is positioned as shown in an image 841 of FIG. 8D, an ultrasound image 843 may be obtained by scanning the pregnant woman's body in the longitudinal direction via the probe 20. The ultrasound image 843 may show a cross-section of the fetus having the same orientation as illustrated in an image 845. The head of the fetus in the ultrasound image 843 may be located left with respect to the torso.

The processor 410 may detect a head of a fetus in a first ultrasound image and determine a direction of the fetus's head based on the detected head. The processor 410 may determine whether the fetus's head in the first ultrasound image is located right or left with respect to the torso. The processor 410 may determine a presentation of the fetus based on a relationship between an orientation of the probe 20 (or a position of a marker being displayed on the display 420) and the direction of the fetus's head.

For example, when a fetus's head detected in an ultrasound image is oriented in a right direction, the processor 410 may determine an orientation of the fetus as corresponding to a vertex presentation of the fetus in the pregnant woman's body. Alternatively, when the fetus's head detected in the ultrasound image is oriented in a left direction, the processor 410 may determine an orientation of the fetus as corresponding to a breech presentation of the fetus in the pregnant woman's body.

The display 420 may display the fetus's head and the direction of the fetus's head on the first ultrasound image. The direction of the fetus's head may be represented by at least one of an image, a figure, a letter, and a symbol.

Figure 9:
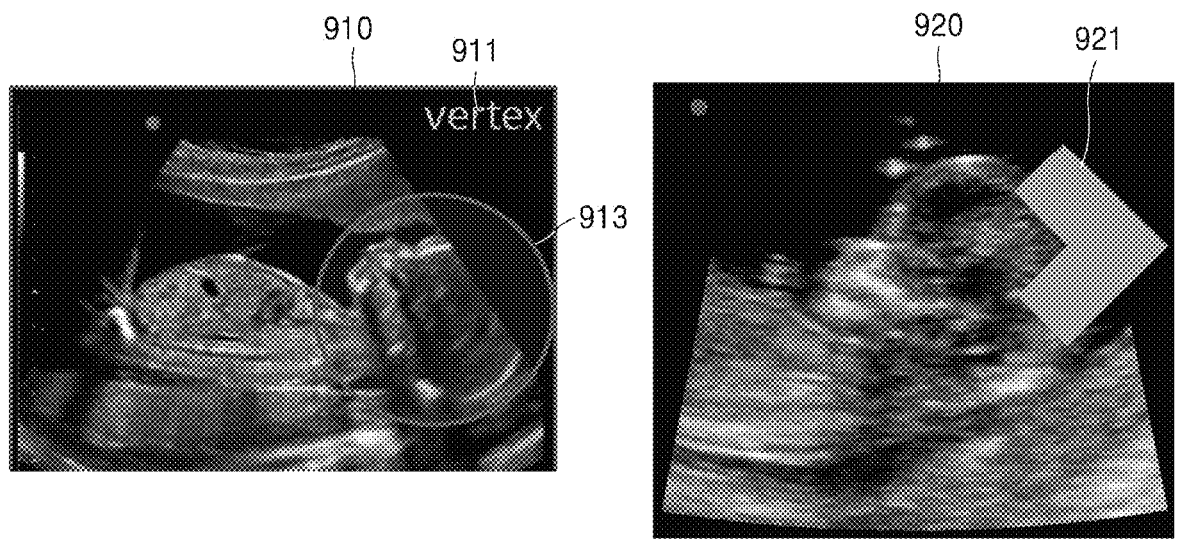
FIG. 9 illustrates an example of an ultrasound image representing a fetus's head and a direction of the fetus's head, according to an embodiment.

FIG. 9 illustrates an example of an ultrasound image representing a fetus's head and a direction of the fetus's head, according to an embodiment.

As shown in a first ultrasound image 910 of FIG. 9, the display 420 may display a detected head 913 of a fetus and show a vertex of the fetus as being located on the right side of the image 910. The display 420 may show the fetus's head in the first ultrasound image 910 as being located right with respect to the torso. As shown in an image 920 of FIG. 9, the display 420 may display an indicator 921 indicating that the head 913 is located on the right side of the image 920.

The processor 410 may control the display 420 to display a UI for guiding the user to scan a pregnant woman's body in a second direction.

Figure 10:
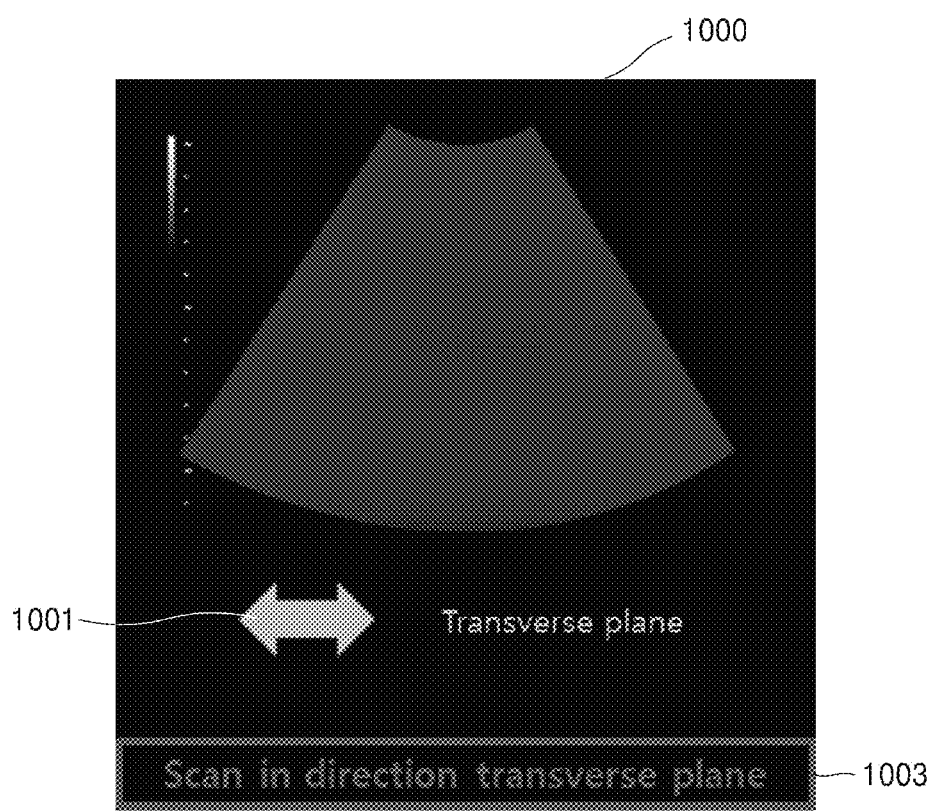
FIG. 10 illustrates a UI displayed by an ultrasound image display apparatus according to an embodiment.

The ultrasound image display apparatus 400 may display a UI for guiding a user through a scanning direction. The scanning direction may be represented by at least one of a letter, an image, and a symbol. For example, referring to FIG. 10, the ultrasound image display apparatus 400 may display an image 1000 having at least one of an arrow 1001 and a guiding phrase 1003 included therein such that a transverse plane of the pregnant woman's body is scanned.

According to guidance by the ultrasound image display apparatus 400, the user may manipulate the probe 20 to scan the transverse plane of the pregnant woman's body.

Figure 11:
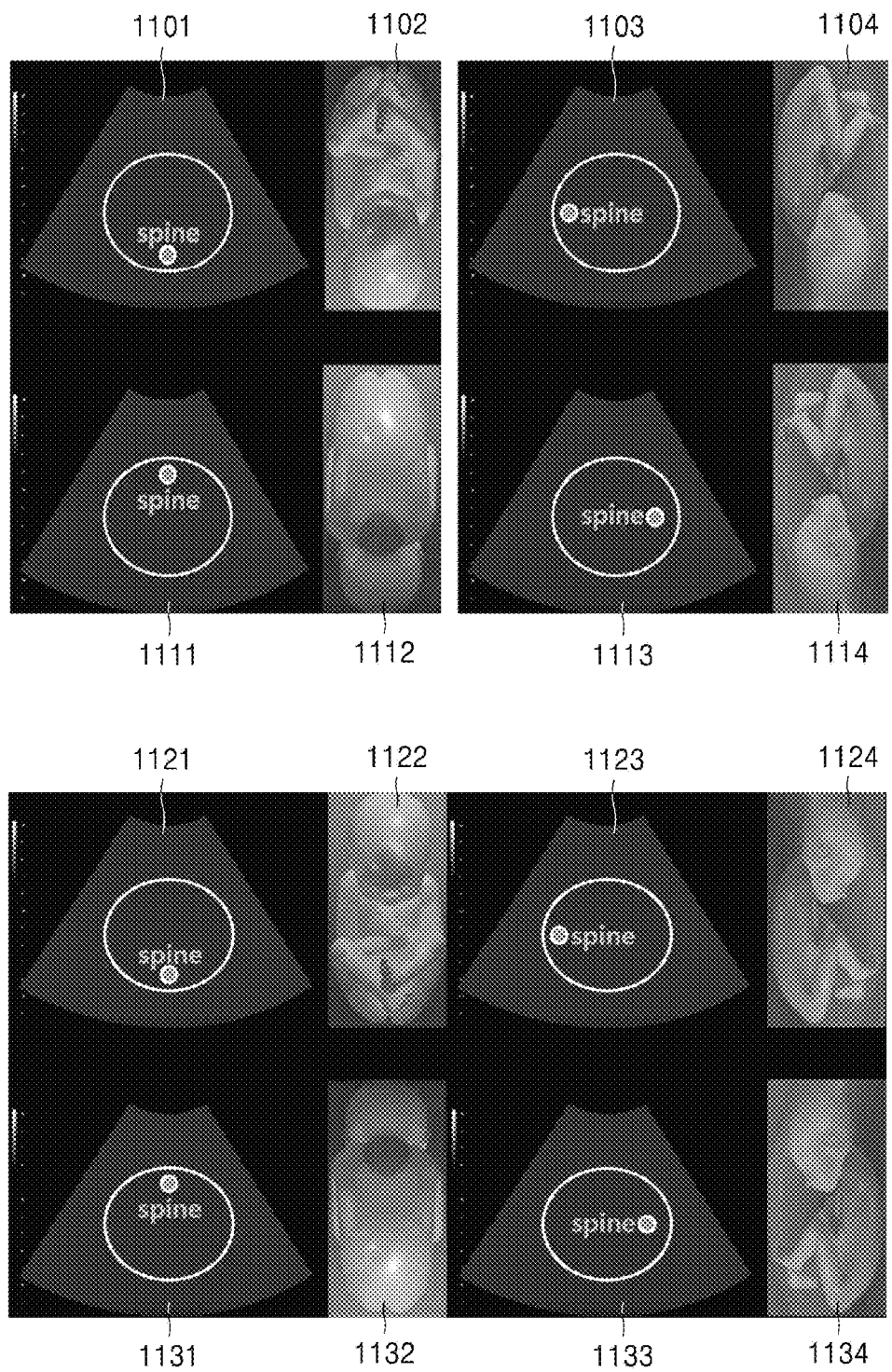
FIG. 11 is a diagram for explaining ultrasound images obtained by scanning according to an orientation of a fetus according to an embodiment.

FIG. 11 is a diagram for explaining ultrasound images obtained by scanning along an orientation of a fetus.

When the fetus is located in a longitudinal direction and a pregnant woman's body is scanned in a transverse direction via the probe 20, as shown in images 1102, 1104, 1112, 1114, 1122, 1124, 1132, and 1134, ultrasound images respectively showing cross-sections of the fetus illustrated in images 1101, 1103, 1111, 1113, 1121, 1123, 1131, and 1133 may be obtained.

For example, when the fetus is positioned as shown in the image 1102 of FIG. 11, an ultrasound image may be obtained by scanning the pregnant woman's body in a transverse direction via the probe 20. When a spine of the fetus faces a pregnant woman's back as shown in the image 1102, the spine may be located at the bottom in the ultrasound image, as shown in the image 1101. A position of the spine detected in a second ultrasound image obtained when the fetus's spine faces the pregnant woman's back may be used as a reference point for determining a rotation angle of the fetus. Alternatively, a point corresponding to the 6 o'clock direction on the ultrasound image or a point corresponding to the bottom of the ultrasound image may be determined as a reference point for determining a rotation angle of the fetus.

As another example, the image 1104 of FIG. 11 shows tan axis of the fetus rotated by 90 degrees compared to the image 1102 of FIG. 11. When the fetus is positioned as shown in the image 1104 of FIG. 11, an ultrasound image showing a cross-section of the fetus illustrated in the image 1103 may be obtained by scanning the pregnant woman's body in the transverse direction via the probe 20. As shown in the image 1103 of FIG. 11, the ultrasound image may be obtained when the fetus's spine is rotated by 90 degrees clockwise with respect to the reference point.

The processor 410 may detect the fetus's spine in the second ultrasound image and determine a direction of the fetus's spine based on the detected fetus's spine. The processor 410 may detect a fetus's torso and spine in the second ultrasound image and determine an angle by which an axis of the fetus in the second ultrasound image rotates relative to the reference point. The display 420 may display the fetus's spine and rotation angle on the second ultrasound image.

According to an embodiment of the disclosure, the ultrasound image display apparatus 400 may acquire an angle by which the fetus rotates within the pregnant woman's body based on a position of the fetus's spine by scanning the pregnant woman's body along a transverse-axis direction.

Figure 12:
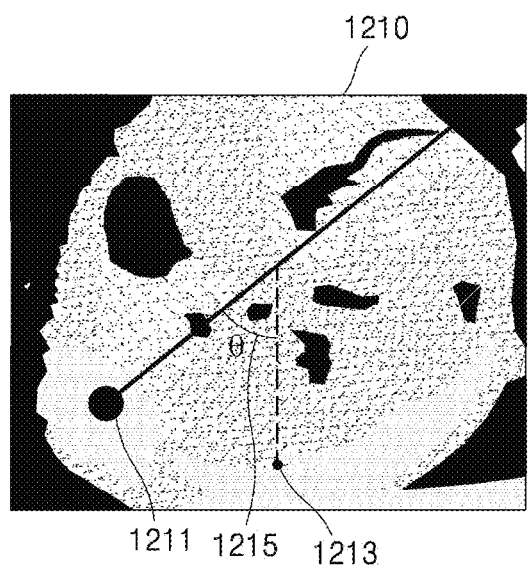
FIG. 12 illustrates an example of an ultrasound image representing a fetus's spine and rotation angle, according to an embodiment.

FIG. 12 illustrates an example of an ultrasound image representing a fetus's spine and rotation angle, according to an embodiment of the disclosure. As shown in an ultrasound image 1210 of FIG. 12, the display 420 may display a fetus's spine 1211 and a rotation angle 1215 of the fetus between a line connecting a central point of a fetus's torso with a reference point 1213 and a line connecting the central point thereof with the fetus's spine 1211.

According to an embodiment of the disclosure, when a fetus's head or spine is not detected in one of first and second ultrasound images, the ultrasound image display apparatus 400 may display a UI for guiding the user to rescan the pregnant woman's body.

When the fetus's head is detected in the first ultrasound image, the processor 410 may determine a direction of the fetus's head by analyzing the first ultrasound image. However, when the fetus's head is not detected in the first ultrasound image, the processor 410 may control the display 420 to display a UI for guiding the user to rescan the pregnant woman's body. The processor 410 may control the display 420 to display a UI for guiding the user to scan the pregnant woman's body in a first direction.

Furthermore, when the fetus's spine is detected in the second ultrasound image, the processor 410 may determine a direction of the fetus's spine analyzing the second ultrasound image. Otherwise, when the fetus's spine is not detected in the second ultrasound image, the processor 410 may control the display 420 to display a UI for guiding the user to rescan the pregnant woman's body. The processor 410 may control the display 420 to display a UI for guiding the user to scan the pregnant woman's body in a second direction.

Figure 13:
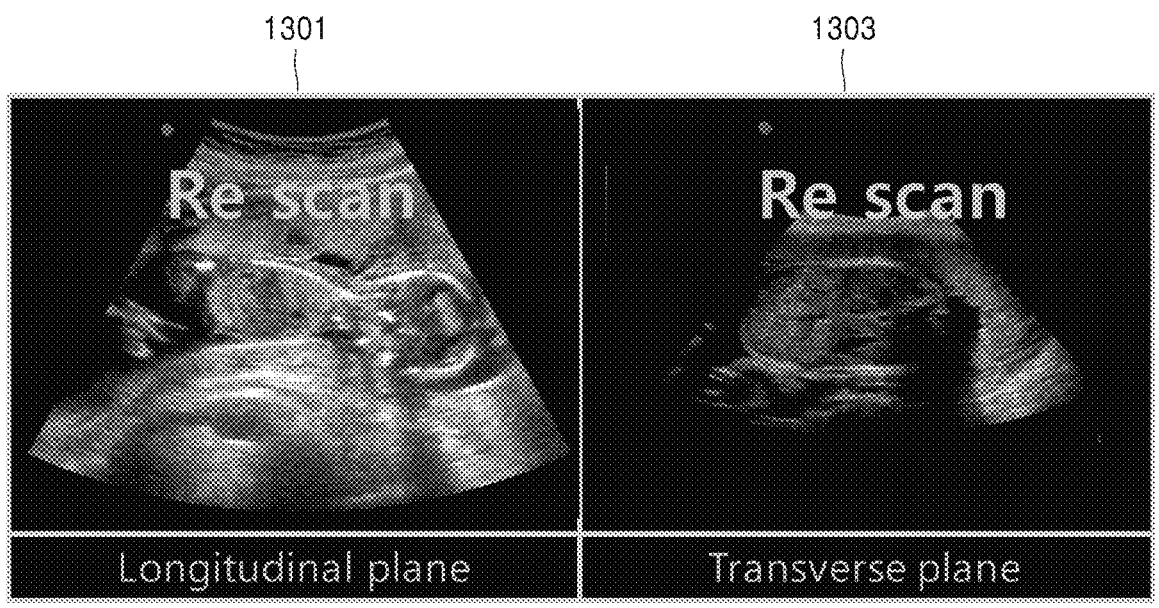
FIGS. 13 and 14 respectively illustrate UIs displayed by an ultrasound image display apparatus, according to an embodiment.

Referring to FIG. 13, the ultrasound image display apparatus 400 may display obtained first and second ultrasound images together on a single screen. However, embodiments of the disclosure are not limited thereto, and the ultrasound image display apparatus 400 may sequentially display the first and second ultrasound images.

As shown in an image 1301 of FIG. 13, according to an embodiment, when a fetus's head is not detected in the first ultrasound image obtained by scanning a pregnant woman's body in a longitudinal plane, the ultrasound image display apparatus 400 may display a UI for guiding the user to rescan the pregnant woman's body. The user may change an orientation, an angle, etc., of the probe 20 based on the UI for guiding rescanning, such that the ultrasound image display apparatus 400 may obtain the first ultrasound image again.

Furthermore, as shown in an image 1303 of FIG. 13, according to an embodiment, when a fetus's spine is not detected in the second ultrasound image obtained by scanning the pregnant woman's body in a transverse plane, the ultrasound image display apparatus 400 may display a UI for guiding the user to rescan the pregnant woman's body. The user may change an orientation, an angle, etc., of the probe 20 based on the UI for guiding rescanning, such that the ultrasound image display apparatus 400 may obtain the second ultrasound image again.

According to an embodiment of the disclosure, when the fetus's head or spine is not detected in one of the first and second ultrasound images, the ultrasound image display apparatus 400 may receive a user input related to an orientation of the fetus.

As shown in FIG. 4B, according to an embodiment, the ultrasound image display apparatus 400 may further include an input interface for receiving a user input.

When the fetus's head is detected in the first ultrasound image, the processor 410 may determine a direction of the fetus's head by analyzing the first ultrasound image. However, when the fetus's head is not detected in the first ultrasound image, the processor 410 may determine the direction of the fetus's head based on a user input with respect to the first ultrasound image.

Furthermore, when the fetus's spine is detected in the second ultrasound image, the processor 410 may determine a direction of the fetus's spine analyzing the second ultrasound image. Otherwise, when the fetus's spine is not detected in the second ultrasound image, the processor 410 may determine the direction of the fetus's head based on a user input with respect to the second ultrasound image.

Figure 14:
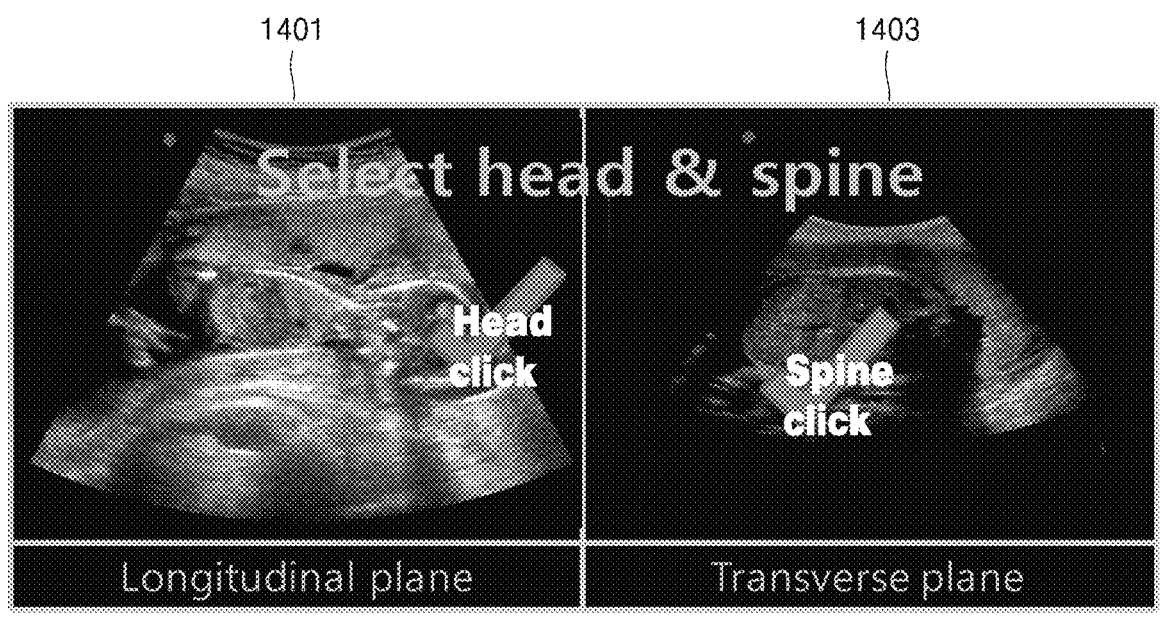

As shown in an image 1401 of FIG. 14, according to an embodiment, when a fetus's head is not detected in a first ultrasound image obtained by scanning a pregnant woman's body in a longitudinal plane, the ultrasound image display apparatus 400 may display a UI for receiving a user input of designating a direction of the fetus's head. The user may designate the direction of the fetus's head determined in the image 1401, based on the UI for guiding the user to designate the direction of the fetus's head.

Furthermore, as shown in an image 1403 of FIG. 14, according to an embodiment, when a fetus's spine is not detected in a second ultrasound image obtained by scanning a pregnant woman's body in a transverse plane, the ultrasound image display apparatus 400 may display a UI for receiving a user input of designating a direction of the fetus's spine. The user may designate the direction of the fetus's spine determined in the image 1403, based on the UI for guiding the user to designate the direction of the fetus's spine.

Figure 15:
FIG. 15 is a diagram for explaining an orientation of a fetus determined based on directions of a fetus's head and spine, according to an embodiment.
Figure 15:
Figure 15:
Figure 15:
Figure 15:
Figure 15:

As shown in a table of FIG. 15, according to an embodiment, the ultrasound image display apparatus 400 may determine an orientation of a fetus within a pregnant woman's body based on directions of a fetus's head and spine.

A first column 1501 of the table of FIG. 15 represents cases in which the fetus is in a longitudinal lie vertex presentation where the vertex of the fetus faces a cervix. A second column 1503 represents cases in which the fetus is in a longitudinal line breech presentation where buttocks of the fetus face the cervix.

The processor 410 may determine whether the fetus is in a longitudinal lie vertex presentation or longitudinal lie breech presentation, based on whether a fetus's head is oriented in the left or right direction in a first ultrasound image obtained by scanning the fetus in a longitudinal plane. When it is assumed that the first ultrasound image is obtained via the probe 20 placed in an orientation corresponding to a marker being displayed on the display 420, the processor 410 may determine the direction of the fetus's head. The processor 410 may identify in advance which of the left side and right side of the first ultrasound image is closer to the cervix. The processor 410 may determine which of the crown and buttocks are closer to the cervix, based on the direction of the fetus's head in the first ultrasound image and the direction of the marker being displayed (or the orientation of the probe 20).

A first row 1505 of the table of FIG. 15 represents cases in which the fetus is in a presentation wherein the fetus's spine faces the pregnant woman's back. Second through fourth rows 1506, 1507, and 1509 respectively represent cases in which the fetus is in a presentation where an axis of the fetus rotates 90, 180, and 270 degrees in a clockwise direction.

The processor 410 may determine an angle by which the axis of the fetus rotates from a second ultrasound image obtained by scanning the fetus in a transverse plane. When it is assumed that the second ultrasound image is obtained via the probe 20 placed in an orientation corresponding to a marker being displayed on the display 420, the processor 410 may determine the direction of the fetus's spine. The processor 410 may determine the angle by which the axis of the fetus rotates based on the direction of the fetus's spine.

The processor 410 may also determine an orientation of the fetus within the pregnant woman's body based on the directions of the fetus's head and spine.

Figure 16:
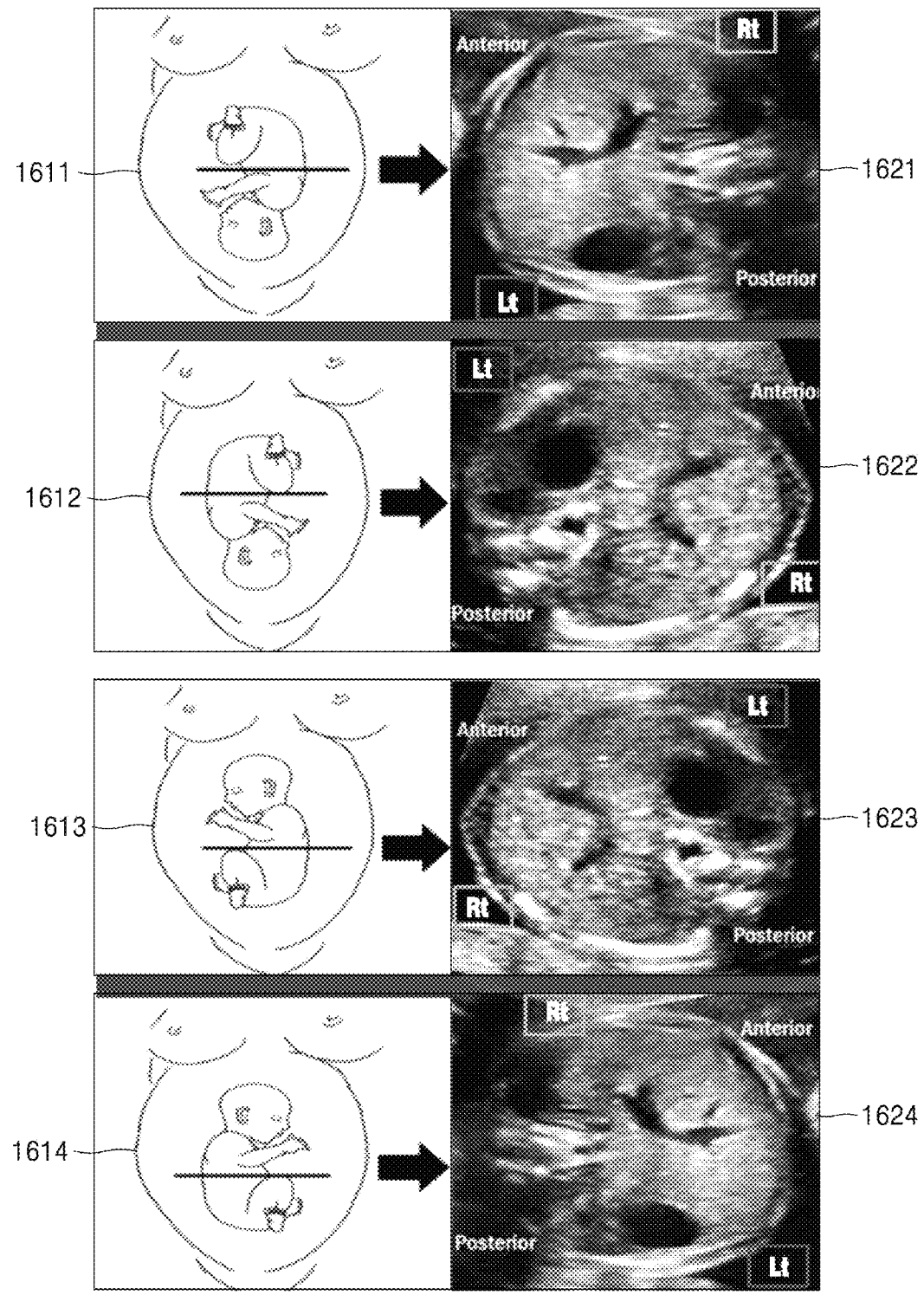
FIG. 16 illustrates an example of an ultrasound image representing left and right sides of a fetus, according to an embodiment.

FIG. 16 illustrates an example of an ultrasound image representing left and right sides of a fetus being displayed, according to an embodiment of the disclosure. Ultrasound images 1621 through 1624 may be obtained by scanning a pregnant woman's body in a second direction (e.g., a transverse direction). As shown in FIG. 16, information about left and right orientations of the fetus, which is indicated on the ultrasound images 1621 through 1624 respectively showing transverse planes of the fetus, may vary according to whether a presentation of the fetus is a vertex presentation (1611 and 1622) or a breech presentation (1613 and 1614). In each of the ultrasound images 1621 through 1624, "Lt' and "Rt' respectively indicate left and right sides of the fetus.

As described above, according to various embodiments of the disclosures, the ultrasound image display apparatus 400 may scan a fetus in a direction of a longitudinal or transverse plane of a pregnant woman's body and detect a region corresponding to a distinctive structure (e.g., a head, a spine, or the like), thereby providing information about an orientation of the fetus determined based on the detected region. Accordingly, the user may easily check information about the left and right sides of the fetus and intuitively determine whether arrangement of organs of the fetus is normal or abnormal based on the information about the left and right sides of the fetus.

Figure 17A:
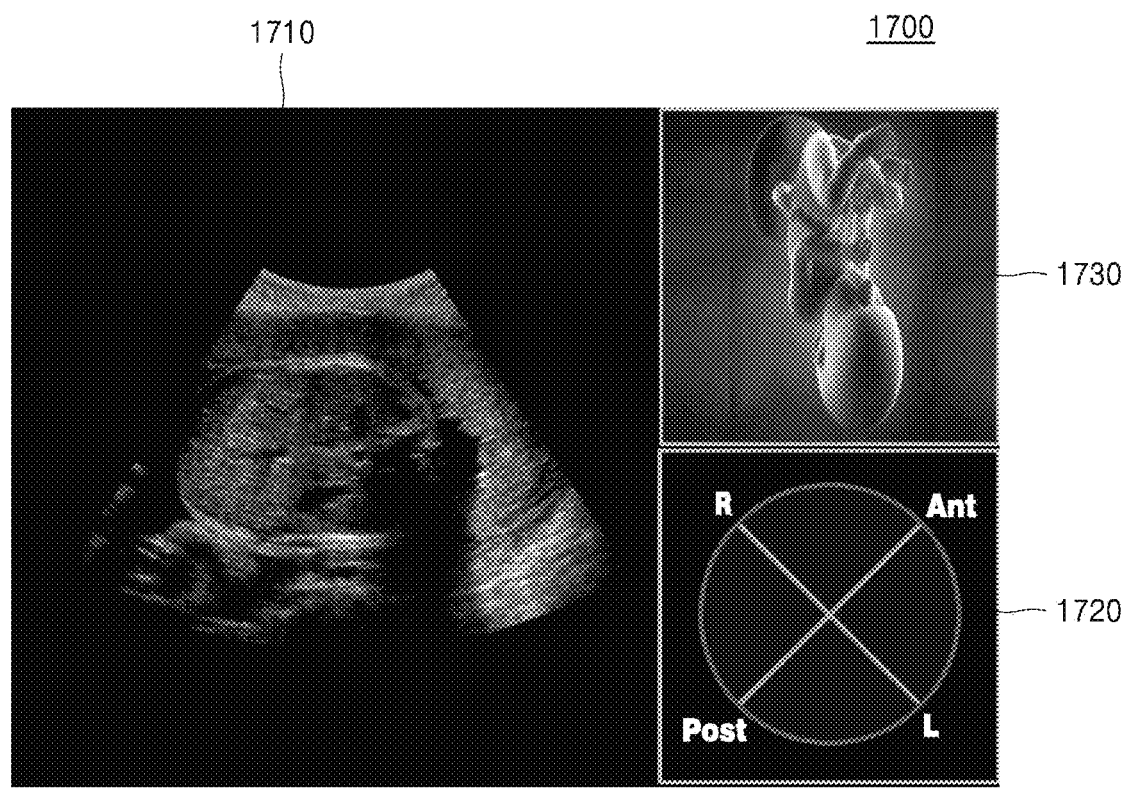
FIGS. 17A and 17B illustrate screens displayed by an ultrasound image display apparatus, according to an embodiment.
Figure 17B:
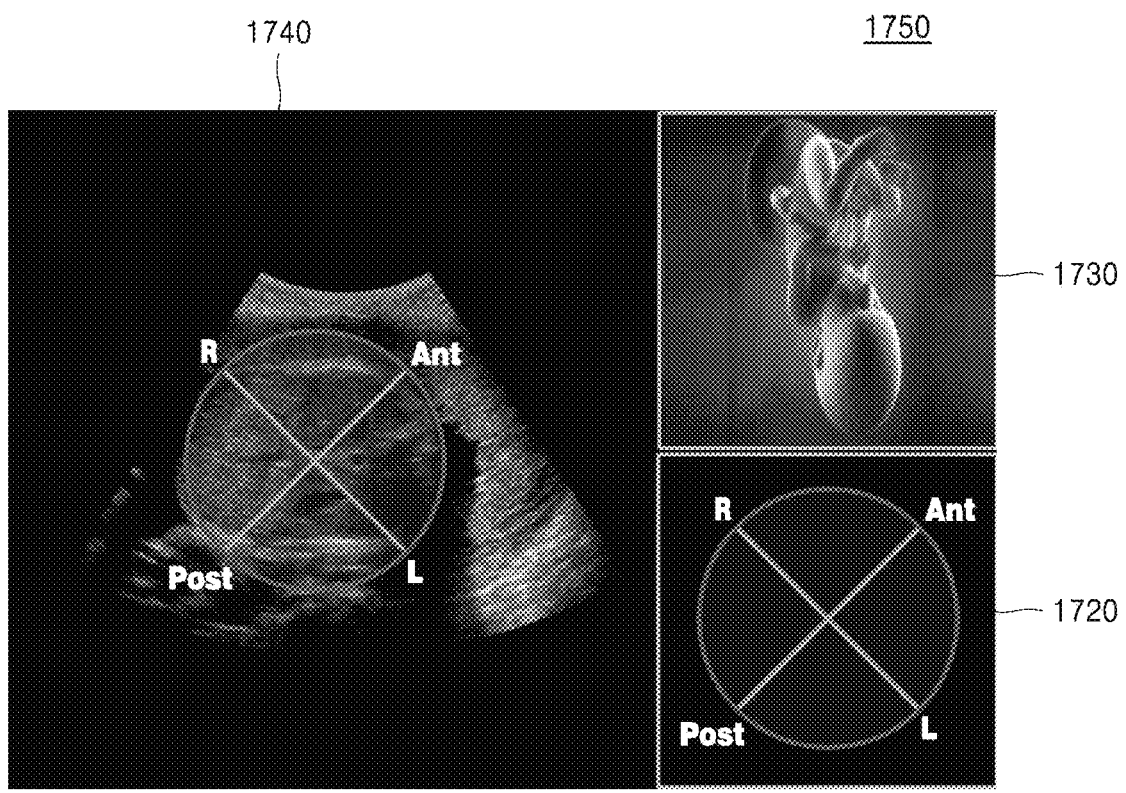

An image representing an orientation of the fetus, which is displayed on the display 420, may include at least one of an image having indicated thereon at least one of the left and right sides of the fetus in an ultrasound image, an image showing a cross-section and the left and right sides of the fetus in the ultrasound image, and a mimic image showing the fetus three-dimensionally based on an orientation of the fetus. FIGS. 17A and 17B illustrate screens 1700 and 1750 displayed by an ultrasound image display apparatus, according to an embodiment of the disclosure.

As seen on the screen 1700 of FIG. 17A, according to an embodiment of the disclosure, the ultrasound image display apparatus 400 may display images 1720 and 1730 representing an orientation of a fetus, together with an ultrasound image 1710 obtained by scanning a pregnant woman's body. The image 1720 shows a cross-section and left and right sides of the fetus in the ultrasound image 1710. The image 1730 is a mimic image showing the fetus three-dimensionally based on the orientation of the fetus.

As seen on the screen 1750 of FIG. 17B, the ultrasound image display apparatus 400 may display an image 1740 obtained by overlaying an image 1720 representing an orientation of the fetus on the ultrasound image 1710 obtained by scanning the pregnant woman's body.

According to an embodiment of the disclosure, when the orientation of the fetus is represented using a mimic image, the processor 410 of the ultrasound image display apparatus 400 may control the display 420 to rotate the mimic image based on a user input.

Figure 18A:
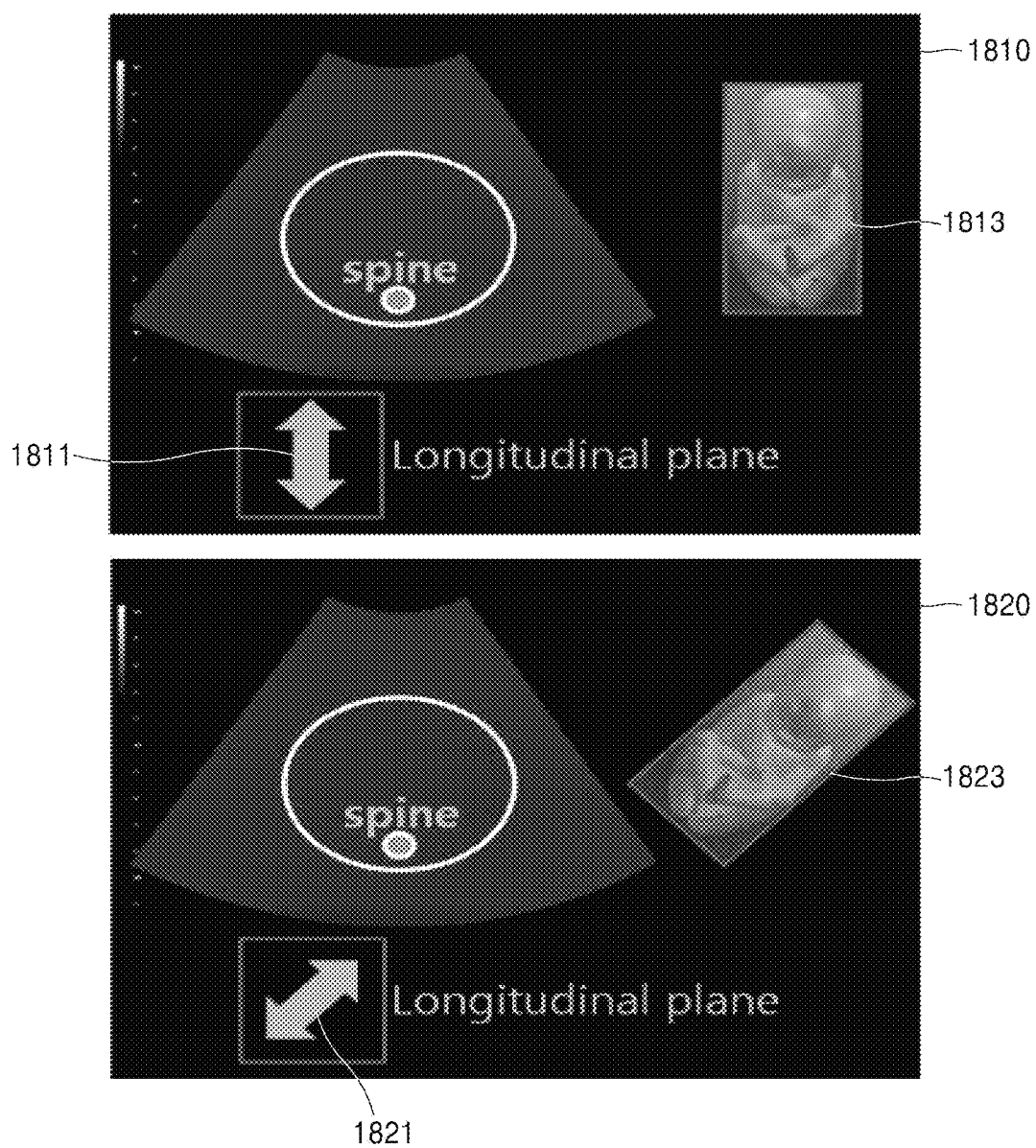
FIG. 18A is a diagram for explaining a method, performed by an ultrasound image display apparatus, of rotating and displaying a mimic image, according to an embodiment.

As seen on a screen 1810 of FIG. 18A, in general, a pregnant woman's body may be scanned in a longitudinal direction in order to scan a fetus in a longitudinal plane. An arrow 1811 may indicate a general longitudinal scan, and a mimic image 1813 may represent an orientation of the fetus within the pregnant woman's body. However, as seen on a screen 1820 of FIG. 18A, when the fetus is lying obliquely within the pregnant woman's body, the fetus may be scanned in a longitudinal plane obliquely to the pregnant woman's body by taking into account a direction in which the fetus is lying. The processor 410 may set a scanning direction based on a user input, as indicated by an arrow 1821. The processor 410 may control the display 420 such that a direction of a mimic image 1823 may change as the scanning direction changes. It can be seen that the mimic image 1823 is rotated compared to the mimic image 1813.

Thus, according to an embodiment of the disclosure, the ultrasound image display apparatus 400 may provide an accurate mimic image by taking into account an orientation of a fetus within a pregnant woman's body.

Furthermore, according to an embodiment of the disclosure, when the orientation of the fetus is represented using a mimic image, the processor 410 of the ultrasound image display apparatus 400 may adjust an ultrasound image being displayed based on a user input with respect to the mimic image. For example, the processor 410 may enlarge, reduce, pan and/or rotate an ultrasound image based on a user input.

Figure 18B:
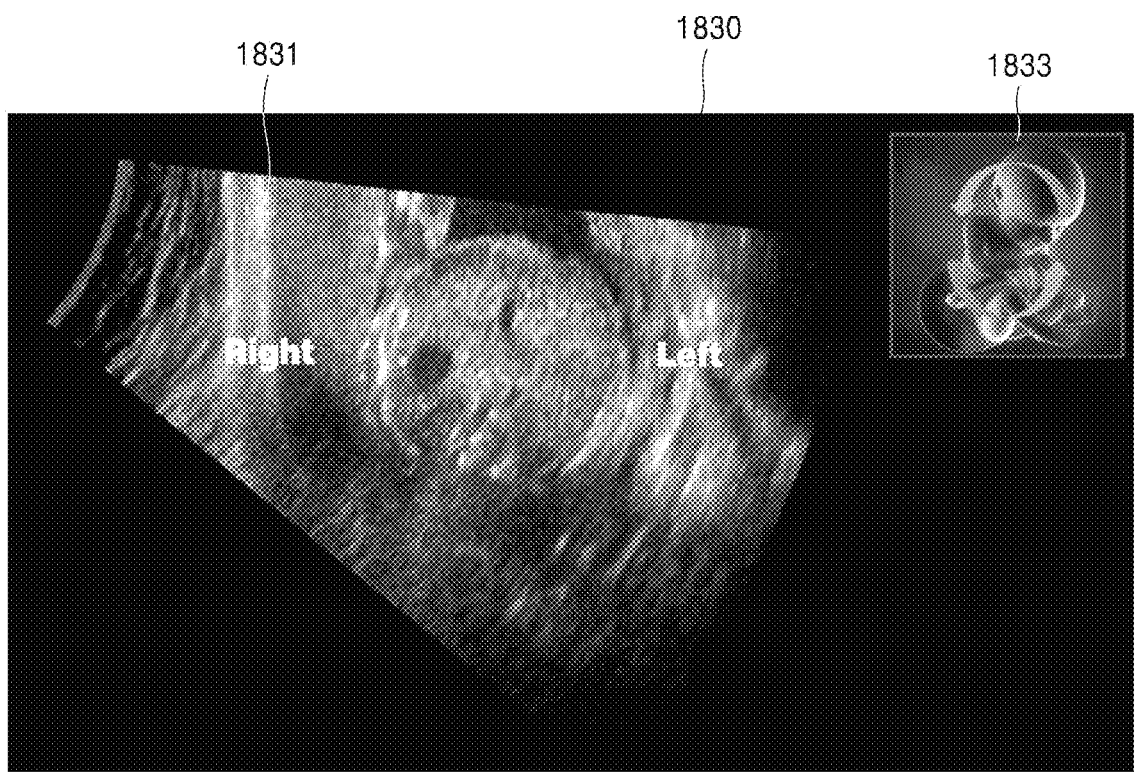
FIG. 18B is a diagram for explaining a method, performed by an ultrasound image display apparatus, of rotating an ultrasound image based on a user input with respect to a mimic image and displaying the resulting ultrasound image, according to an embodiment.

As seen on a screen 1830 of FIG. 18B, the ultrasound image display apparatus 400 may rotate an ultrasound image 1831 based on a user input of rotating a mimic image 1833.

Figure 19A:
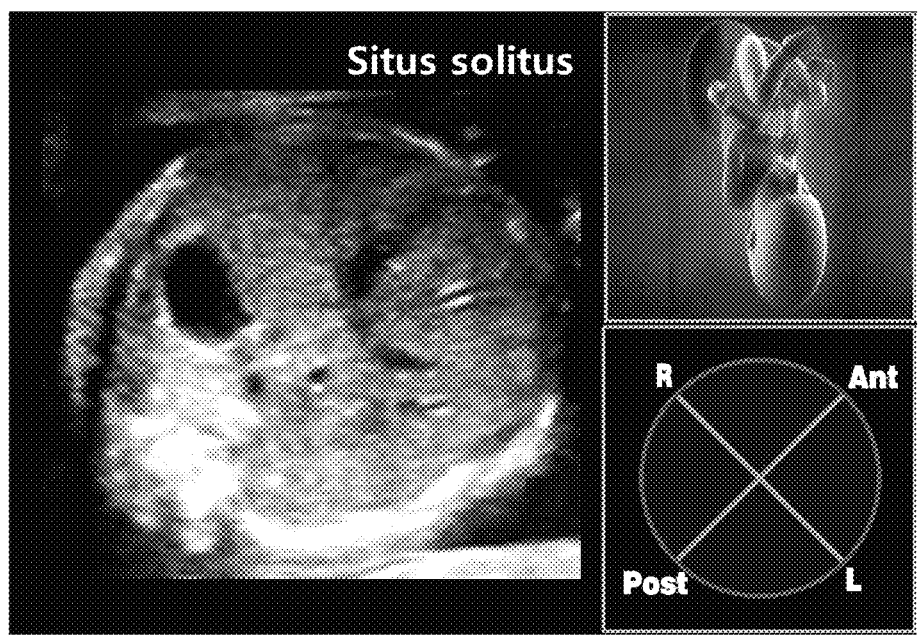
FIGS. 19A and 19B illustrate screens displaying whether locations of organs of a fetus are normal or abnormal, based on information about an orientation of the fetus provided by an ultrasound image display apparatus, according to an embodiment.
Figure 19B:
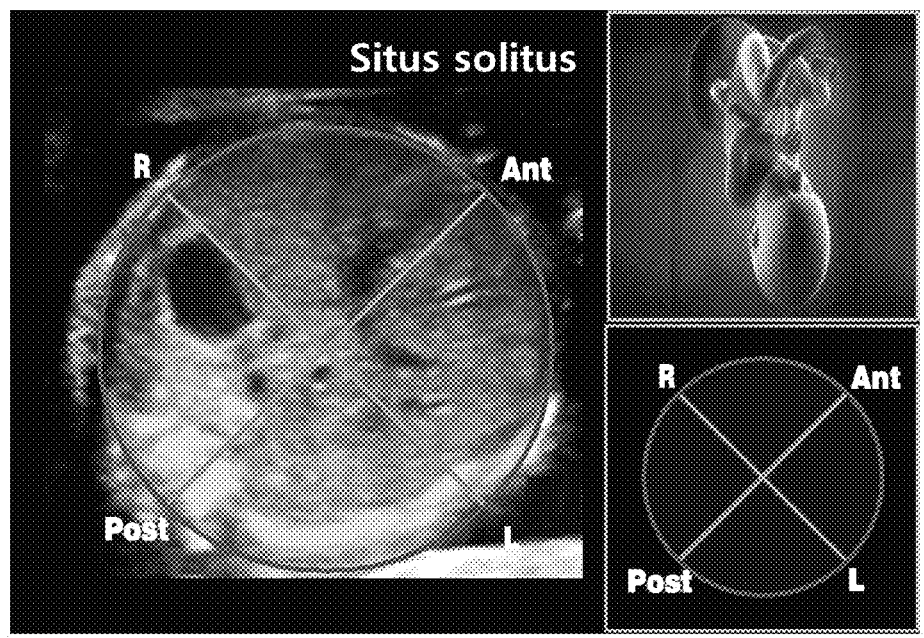

According to an embodiment of the disclosure, the user of the ultrasound image display apparatus 400 may easily identify left and right sides of a fetus based on an image representing an orientation of the fetus and determine whether arrangement of organs of the fetus is situs solitus or situs inversus. The ultrasound image display apparatus 400 may display, based on a user input, whether arrangement of organs of the fetus is situs solitus or situs inversus. For example, as shown in FIG. 19A or 19B, the ultrasound image display apparatus 400 may display arrangement of organs of the fetus as being a normal case in which the organs of the fetus are in the normal position.

Alternatively, the ultrasound image display apparatus 400 may directly identify a position of organs of the fetus based on information about the left and right sides of the fetus. The ultrasound image display apparatus 400 may detect a region corresponding to at least one of the organs of the fetus in an ultrasound image to determine whether the organ of the fetus is in the normal position based on the information about the left and right sides of the fetus. The ultrasound image display apparatus 400 may determine whether arrangement of the organs of the fetus is situs solitus or situs inversus based on the position of the organ of the fetus. For example, as shown in FIG. 19A or 19B, the ultrasound image display apparatus 400 may display arrangement of the organs of the fetus as being a normal case in which the organs of the fetus are in the normal position.

For example, the ultrasound image display apparatus 400 may determine a case in which an organ of a fetus such as the heart is located on the left side of the chest as being situs solitus and a case in which the heart is located on the right side as being situs inversus. By determining whether an organ of the fetus is located on the left or right side in a scanned cross-section, the ultrasound image display apparatus 400 may determine whether arrangement of organs of the fetus is situs solitus or situs inversus. Furthermore, the ultrasound image display apparatus 400 may display information about a determination result on a screen to allow the user to easily recognize the information.

In addition, according to an embodiment of the disclosure, when an orientation of a fetus is represented using a mimic image, the processor 410 of the ultrasound image display apparatus 400 may determine a posture of the fetus based on a fetus's legs detected in an ultrasound image and generate the mimic image based on the orientation and posture of the fetus. The ultrasound image used to detect the fetus's legs may be a first ultrasound image obtained by scanning the fetus in a longitudinal plane.

Figure 20A:
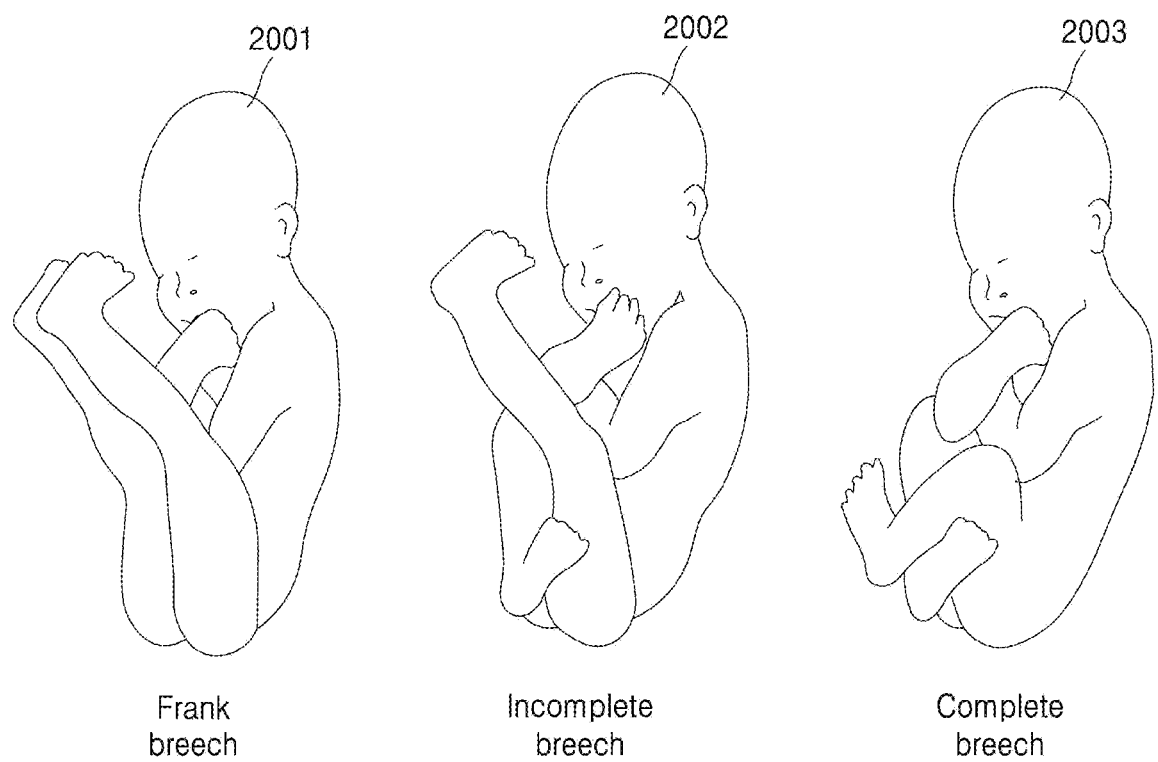
FIGS. 20A, 20B, and 21 are diagrams for explaining a method, performed by an ultrasound image display apparatus, of determining and displaying a fetal posture, according to an embodiment of the disclosure.
Figure 20B:
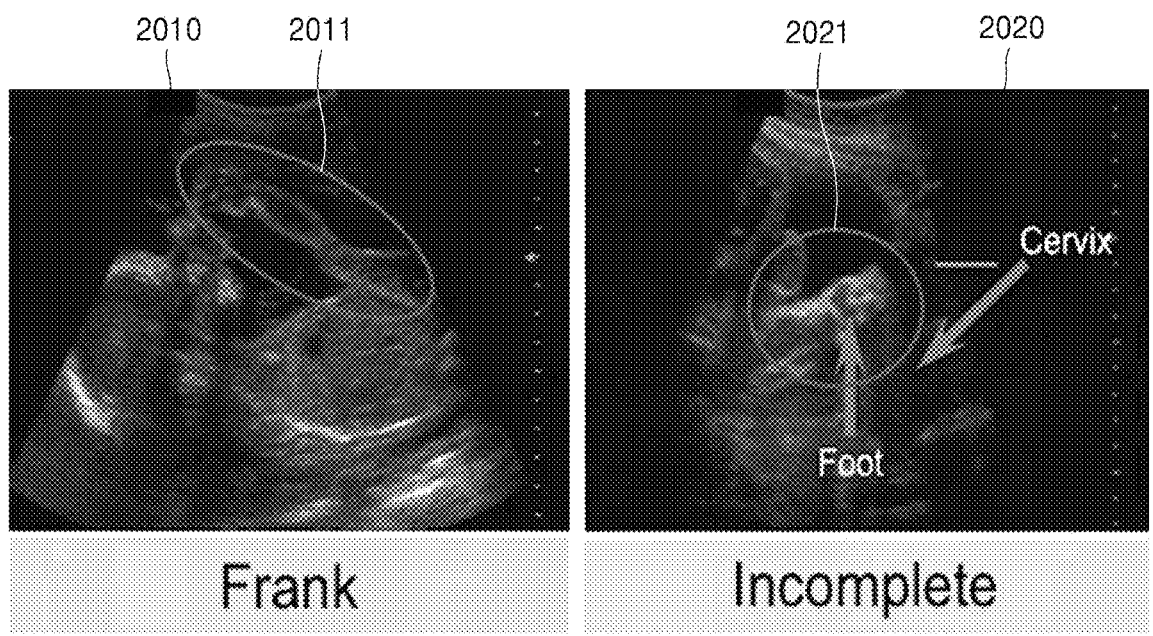
Figure 21:
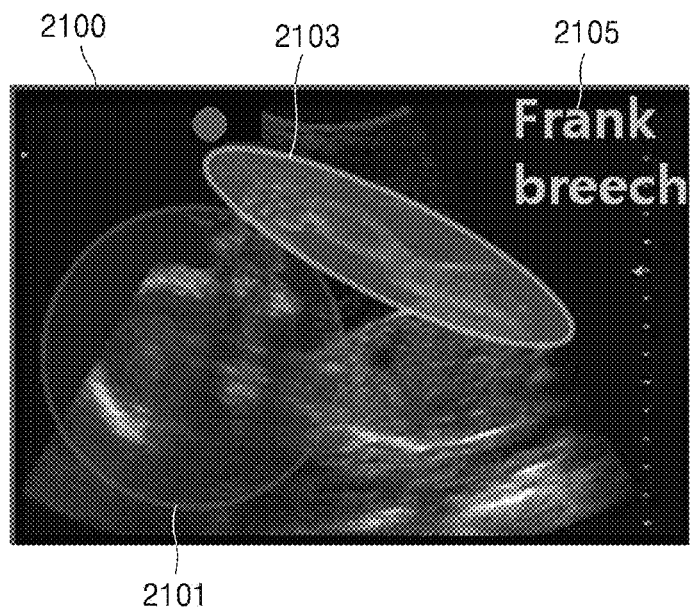

FIGS. 20A, 20B, and 21 are diagrams for explaining a method, performed by an ultrasound image display apparatus, of determining and displaying a fetal posture, according to an embodiment of the disclosure.

As shown in FIG. 20A, a fetus may assume various postures within a pregnant woman's body. An image 2001 represents a frank breech in which the fetus sticks both legs straight up toward its head, and an image 2002 represents an incomplete breech in which one leg of the fetus is down below its buttocks. An image 2003 represents a complete breech in which both legs of the fetus are bent at the knees.

According to an embodiment, the ultrasound image display apparatus 400 may also detect a fetus's leg or foot. As shown in FIG. 20B, according to an embodiment, the ultrasound image display apparatus 400 may determine a type of posture of a fetus based on a position of a fetus's leg and display the determined type of posture on a screen.

Referring to FIG. 20B, the processor 410 of the ultrasound image display apparatus 400 may determine a posture of a fetus as a frank breech based on a fetus's leg 2011 detected in an ultrasound image 2010. Furthermore, the processor 401 may determine the posture of the fetus as an incomplete breech based on a fetus's foot 2021 detected in an ultrasound image 2020.

As shown in FIG. 21, the display 420 of the ultrasound image display apparatus 400 may determine a posture of a fetus as a frank breech based on a fetus's head 2101 and leg 2103 detected in an ultrasound image 2100 and display information 2105 about the determined posture of the fetus on the ultrasound image 2100.

A method, performed by the ultrasound image display apparatus 400, of displaying an image representing an orientation of a fetus together with an ultrasound image according to an embodiment of the disclosure will be described in more detail below. Each operation of methods of FIGS. 22, 23A, and 23B may be performed by at least one component described with reference to FIGS. 4A and 4B. Thus, descriptions that are already provided above with respect to FIGS. 4A and 4B will not be repeated below.

Figure 22:
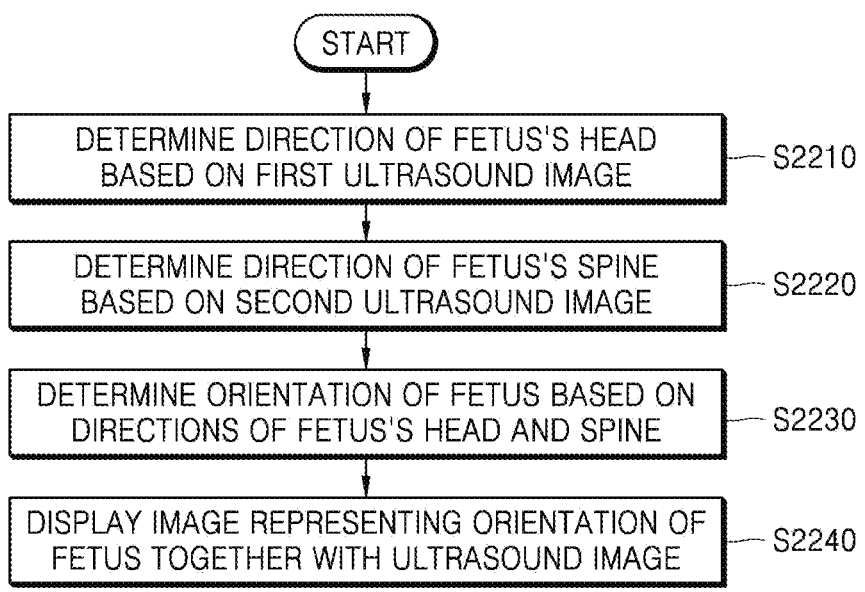
FIG. 22 is a flowchart of a method of displaying an ultrasound image, according to an embodiment.

FIG. 22 is a flowchart of a method of displaying an ultrasound image, according to an embodiment.

According to an embodiment, the ultrasound image display apparatus 400 may determine a direction of a fetus's head based on a first ultrasound image obtained by scanning a pregnant woman's body in a first direction (S2210).

The ultrasound image display apparatus 400 may display a UI for guiding a user to scan a pregnant woman's body in a first direction, obtain a first ultrasound image, and detect a fetus's head in the first ultrasound image. For example, the first direction may be a longitudinal direction.

The ultrasound image display apparatus 400 may determine a presentation of the fetus based on a relationship between an orientation of the probe 20 (or a position of a marker being displayed) and a direction of the fetus's head. In detail, when at least a portion of the fetus's head and at least a portion of the fetus's buttocks are both identified in the first ultrasound image, the ultrasound image display apparatus 400 may determine a direction of the fetus's head. Alternatively, when at least a portion of the fetus's head or at least a portion of the fetus's buttocks is identified in the first ultrasound image, the ultrasound image display apparatus 400 may determine a direction of the fetus's head. The ultrasound image display apparatus 400 may determine whether a presentation of the fetus is a vertex presentation or a breech presentation based on the direction of the fetus's head.

When the fetus's head is not detected in the first ultrasound image, the ultrasound image display apparatus 400 may display a UI for guiding the user to rescan the pregnant woman's body. The ultrasound image display apparatus 400 may detect a fetus's head in a first ultrasound image obtained by rescanning the pregnant woman's body and determine a direction of the fetus's head based on the first ultrasound image.

Alternatively, when the fetus's head is not detected in the first ultrasound image, the ultrasound image display apparatus 400 may determine a direction of the fetus's head based on a user input.

When the fetus's head is detected in the first ultrasound image, the ultrasound image display apparatus 400 may determine whether the fetus's head in the first ultrasound image is located right or left with respect to the torso. The ultrasound image display apparatus 400 may display the fetus's head and a direction of the fetus's head on the first ultrasound image. For example, when a fetus's head detected in an ultrasound image is oriented in the right direction, the ultrasound image display apparatus 400 may determine that the fetus is positioned within the pregnant woman's body in a vertex presentation. When the fetus's head detected in the ultrasound image is oriented in the left direction, the ultrasound image display apparatus 400 may determine that the fetus is positioned with the pregnant woman's body in a breech presentation.

According to an embodiment, the ultrasound image display apparatus 400 may determine a direction of a fetus's spine based on a second ultrasound image obtained by scanning the pregnant woman's body in a second direction (S2220).

The ultrasound image display apparatus 400 may display a UI for guiding the user to scan a pregnant woman's body in a second direction, obtain a second ultrasound image, and detect a fetus's spine in the second ultrasound image. For example, the second direction may be perpendicular to the first direction. The second direction may be a transverse direction.

When the fetus's spine is detected in the second ultrasound image, the ultrasound image display apparatus 400 may determine a direction of the fetus's spine.

When the fetus's spine is not detected in the second ultrasound image, the ultrasound image display apparatus 400 may display a UI for guiding the user to rescan the pregnant woman's body. The ultrasound image display apparatus 400 may detect a fetus's spine in a second ultrasound image obtained by rescanning the pregnant woman's body and determine a direction of the fetus's spine based on the second ultrasound image.

Alternatively, when the fetus's spine is not detected in the second ultrasound image, the ultrasound image display apparatus 400 may determine a direction of the fetus's spine based on a user input.

When a direction of the fetus's spine is determined, the ultrasound image display apparatus 400 may detect at least one of a fetus's torso and spine in the second ultrasound image. The ultrasound image display apparatus 400 may calculate an angle at which the fetus turns within the pregnant woman's body based on a position of the detected fetus's spine. The ultrasound image display apparatus 400 may determine an angle of rotation of an axis of the fetus relative to a reference point in the second ultrasound image. The ultrasound image display apparatus 400 may also display the fetus's spine and the rotation angle on the second ultrasound image.

Although it is described that the fetus's head and spine are respectively detected in longitudinal and transverse plane images of the pregnant woman's body in operation S2210 and S2220, embodiments of the disclosure are not limited to the example shown in FIG. 22. The fetus's spine may be detected earlier than the fetus's head, and an ultrasound image obtained by scanning the pregnant woman's body in a transverse plane may be acquired prior to acquiring an ultrasound image obtained by scanning the pregnant woman's body in a longitudinal plane.

For example, when the fetus is positioned within the pregnant woman's body in a shoulder presentation as shown in the image 303 of FIG. 3A, the ultrasound image display apparatus 400 may detect a spine of the fetus in a longitudinal plane image of the pregnant woman's body and then its head in a transverse plane image of the pregnant woman's body.

According to an embodiment, the ultrasound image display apparatus 400 may determine an orientation of the fetus within the pregnant woman's body based on the directions of the fetus's head and spine (S2230).

According to an embodiment, the ultrasound image display apparatus 400 may display an image representing the orientation of the fetus, together with an ultrasound image obtained by scanning the pregnant woman's body (S2240).

The ultrasound image display apparatus 400 may display an image representing an orientation of the fetus, together with a real-time ultrasound image obtained by scanning the pregnant woman's body in the second direction. The ultrasound image display apparatus 400 may display information about left and right orientations of the fetus on a cross-section scanned in real-time.

The image representing the orientation of the fetus may include at least one of an image having indicated thereon at least one of the left and right sides of the fetus in an ultrasound image, an image showing a cross-section and the left and right sides of the fetus in the ultrasound image, and a mimic image showing the fetus three-dimensionally based on an orientation of the fetus.

For example, the ultrasound image display apparatus 400 may generate a mimic image based on an angle of rotation of the fetus with respect to a longitudinal axis of the pregnant woman's body and an angle of rotation of the fetus with respect to a transverse axis thereof and provide the generated mimic image, thereby allowing accurate representation of the orientation of the fetus within the pregnant woman's body.

In a scanned cross-section other than cross-sections respectively corresponding to the first and second ultrasound images, the ultrasound image display apparatus 400 may determine whether arrangement of organs of the fetus is situs solitus or situs inversus by using information about left and right sides of the fetus.

According to an embodiment, when an object is scanned via the probe 20, the ultrasound image display apparatus 400 may display a marker representing an orientation of the probe 20 on a screen. The ultrasound image display apparatus 200 may analyze an ultrasound image based on an assumption that an ultrasound image is obtained via the probe 20 placed in a direction corresponding to the marker being displayed. The ultrasound image display apparatus 400 may determine an orientation of the fetus based on directions of the fetus's head and spine and the orientation of the probe 20.

According to an embodiment, the ultrasound image display apparatus 400 may rotate a mimic image based on a user input. The ultrasound image display apparatus 400 may display an ultrasound image that rotates as the mimic image rotates.

According to an embodiment, the ultrasound image display apparatus 400 may further detect a fetus's leg and/or foot in an ultrasound image and determine a type of posture of the fetus based on the detected fetus's leg and/or foot. The ultrasound image display apparatus 400 may generate a mimic image based on the orientation and posture of the fetus and display the generated mimic image. An ultrasound image used as a reference in determining the posture of the fetus may be obtained by scanning the fetus in a longitudinal direction. The ultrasound image display apparatus 400 may display information about the posture of the fetus on the screen.

Figure 23A:
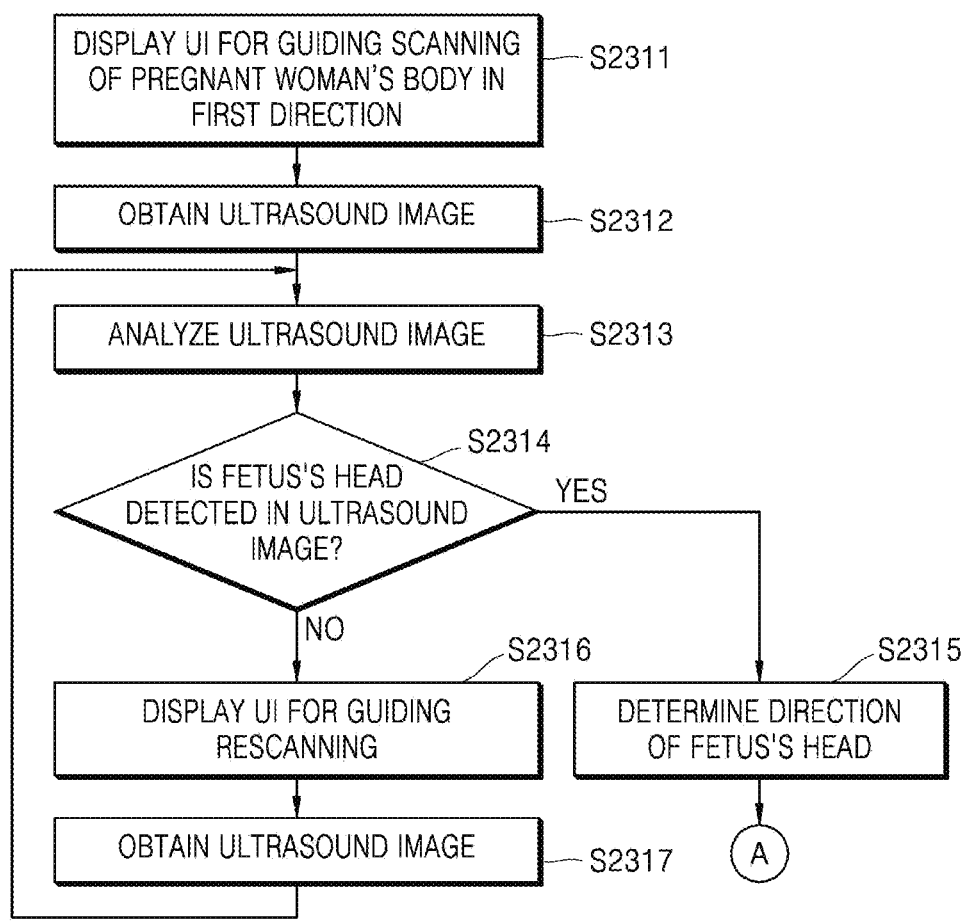
FIGS. 23A and 23B are flowcharts of a method of displaying an ultrasound image, according to an embodiment.
Figure 23B:
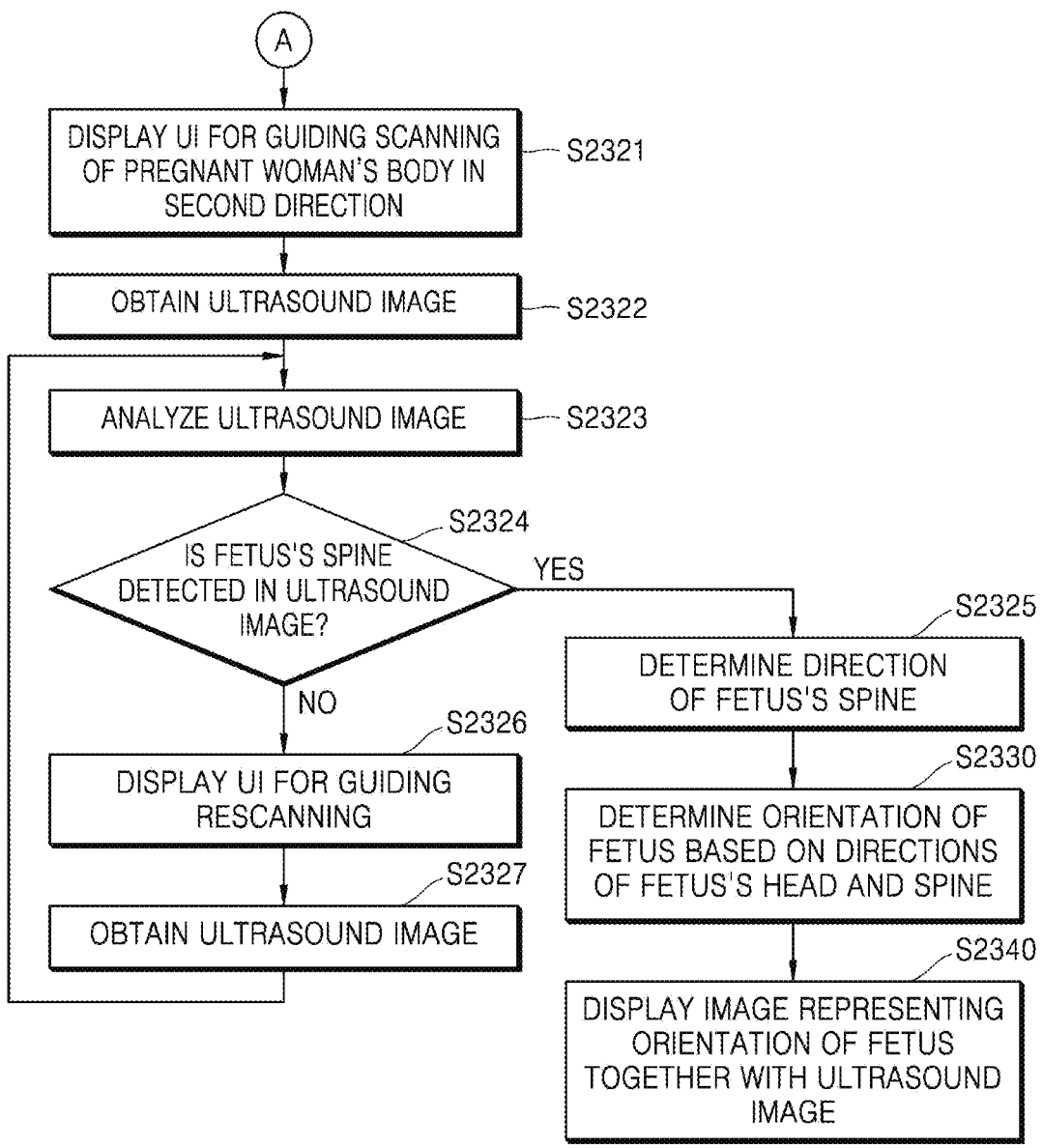

FIGS. 23A and 23B are flowcharts of a method of displaying an ultrasound image, according to an embodiment of the disclosure.

The ultrasound image display apparatus 400 may display a UI for guiding scanning of a pregnant woman's body in a first direction (S2311). A user may place the probe 20 on the pregnant woman's body based on the UI.

The ultrasound image display apparatus 400 may obtain an ultrasound image (S2312). The ultrasound image may be obtained by scanning the pregnant woman's body in the first direction.

The ultrasound image display apparatus 400 may analyze the obtained ultrasound image (S2313). The ultrasound image display apparatus 400 may detect a distinctive structure (e.g., a head, a spine, legs, etc.) of a fetus in the obtained ultrasound image.

The ultrasound image display apparatus 400 may determine whether a fetus's head is detected in the ultrasound image (S2314).

When the fetus's head is detected in the ultrasound image, the ultrasound image display apparatus 400 may determine a direction of the fetus's head (S2315).

Otherwise, when the fetus's head is not detected in the ultrasound image, the ultrasound image display apparatus 400 may display a UI for guiding rescanning of the pregnant woman's body (S2316). The ultrasound image display apparatus 400 may obtain an ultrasound image by rescanning the pregnant woman's body (S2317) and returns to operation S2313 to analyze the ultrasound image.

The ultrasound image display apparatus 400 may display a UI for guiding scanning of the pregnant woman's body in a second direction (S2321). The user may place the probe 20 on the pregnant woman's body based on the UI.

The ultrasound image display apparatus 400 may obtain an ultrasound image (S2322). The ultrasound image display apparatus 400 may analyze the obtained ultrasound image (S2323). The ultrasound image display apparatus 400 may detect a distinctive structure (e.g., a head, a spine, legs, etc.) of the fetus in the obtained ultrasound image.

The ultrasound image display apparatus 400 may determine whether a fetus's spine is detected in the ultrasound image (S2324).

When the fetus's spine is detected in the ultrasound image, the ultrasound image display apparatus 400 may determine a direction of the fetus's spine (S2325). Otherwise, when the fetus's spine is not detected in the ultrasound image, the ultrasound image display apparatus 400 may display a UI for guiding rescanning of the pregnant woman's body (S2326). The ultrasound image display apparatus 400 may obtain an ultrasound image by rescanning the pregnant woman's body (S2327) and returns to operation S2323 to analyze the ultrasound image.

The ultrasound image display apparatus 400 may determine an orientation of the fetus based on the directions of the fetus's head and spine (S2330). The ultrasound image display apparatus 400 may display an image representing the orientation of the fetus, together with the ultrasound image (S2340).

According to embodiments of the disclosure, by displaying an image representing an orientation of a fetus within a pregnant woman's body together with an ultrasound image, it is possible to easily and accurately determine a position of organs inside the fetus.

The embodiments of the disclosure may be implemented as a software program including instructions stored in computer-readable storage media.

A computer may refer to a device capable of retrieving instructions stored in the computer-readable storage media and performing operations according to embodiments of the disclosure in response to the retrieved instructions, and may include ultrasound diagnosis apparatuses according to the embodiments of the disclosure.

The computer-readable storage media may be provided in the form of non-transitory storage media. In this case, the term 'non-transitory' only means that the storage media do not include signals and are tangible, and the term does not distinguish between data that is semi-permanently stored and data that is temporarily stored in the storage media.

In addition, ultrasound image display methods according to embodiments of the disclosure may be included in a computer program product when provided. The computer program product may be traded, as a commodity, between a seller and a buyer.

The computer program product may include a software program and a computer-readable storage medium having stored thereon the software program. For example, the computer program product may include a product (e.g. a downloadable application) in the form of a software program electronically distributed by a manufacturer of an ultrasound diagnosis apparatus or through an electronic market (e.g., Google Play Store™, and App Store™). For such electronic distribution, at least a part of the software program may be stored on the storage medium or may be temporarily generated. In this case, the storage medium may be a storage medium of a server of the manufacturer, a server of the electronic market, or a relay server for temporarily storing the software program.

In a system consisting of a server and a terminal (e.g., an ultrasound diagnosis apparatus), the computer program product may include a storage medium of the server or a storage medium of the terminal. Alternatively, in a case where a third device (e.g., a smartphone) is connected to the server or terminal through a communication network, the computer program product may include a storage medium of the third device. Alternatively, the computer program product may include a software program that is transmitted from the server to the terminal or the third device or that is transmitted from the third device to the terminal.

In this case, one of the server, the terminal, and the third device may execute the computer program product to perform the methods according to embodiments of the disclosure. Alternatively, two or more of the server, the terminal, and the third device may execute the computer program product to perform the methods according to the embodiments of the disclosure in a distributed manner.

For example, the server (e.g., a cloud server, an artificial intelligence (AI) server, or the like) may run the computer program product stored therein to control the terminal communicating with the server to perform the methods according to the embodiments of the disclosure.

As another example, the third device may execute the computer program product to control the terminal communicating with the third device to perform the methods according to the embodiments of the disclosure. In detail, the third device may remotely control an ultrasound diagnosis apparatus to transmit ultrasound signals to an object and generate an ultrasound image of an inner part of the object based on information about signals reflected from the object.

As another example, the third device may run a computer program product to directly perform methods according to embodiments of the disclosure based on a value input from an auxiliary device (e.g., a probe for medical equipment). In detail, the auxiliary device may transmit ultrasound signals to an object and acquire ultrasound signals reflected from the object. The third device may receive information about the reflected ultrasound signals from the auxiliary device and generate an image of an inner part of the object based on the received information.

In a case where the third device executes the computer program product, the third device may download the computer program product from the server and execute the downloaded computer program product. Alternatively, the third device may execute the computer program product that is pre-loaded therein to perform the methods according to the embodiments of the disclosure.

What is claimed is:

1. A method of displaying an ultrasound image, the method comprising:
    determining a direction of a fetus, wherein the determining of the direction of the fetus includes determining a direction of the fetus's head based on a first ultrasound image obtained by scanning a pregnant woman's body in a first direction, and determining a direction of the fetus's spine based on a second ultrasound image obtained by scanning the pregnant woman's body in a second direction;
    determining an orientation of the fetus within the pregnant woman's body based on the directions of the fetus's head and the fetus's spine, wherein the orientation of the fetus is an orientation of an axis of the fetus relative to the pregnant woman's body;
    displaying an image representing the orientation of the fetus together with an ultrasound image obtained by scanning the pregnant woman's body,
    wherein the image representing the orientation of the fetus is displayed together with the ultrasound image obtained by scanning the pregnant woman's body without a mark indicating the direction of the fetus
    displaying on a screen a display marker indicating an orientation of a probe for scanning the pregnant woman's body to obtain the ultrasound image,
    wherein the determining of the orientation of the fetus comprises determining the orientation of the fetus based on the direction of the fetus's head, the direction of the fetus's spine, and the orientation of the probe, wherein a probe marker is attached to one surface of the probe, and
    wherein the scanning of the pregnant woman's body for determining the direction of the fetus's head comprises scanning the pregnant woman's body based on a position of the probe marker and a position of the display marker with respect to the first ultrasound image on the screen, and
    determining by a processor, whether the fetus's head in the first ultrasound image is located right or left with respect to the fetus's torso, and if the fetus's head detected in the first ultrasound image is oriented in a right direction, the processor determines the orientation of the fetus as corresponding to a vertex presentation of the fetus in the pregnant woman's body, and if the fetus's head detected in the first ultrasound image is oriented in a left direction, the processor determines the orientation of the fetus as corresponding to a breech presentation of the fetus in the pregnant woman's body, wherein the determining of the direction of the fetus's spine comprises detecting the fetus's spine and the torso of the fetus in the second ultrasound image, determining, based on the fetus's spine and the fetus's torso, an angle of rotation of the axis of the fetus with respect to a reference point, displaying the fetus's spine and the angle of rotation on the second ultrasound image, and determining the fetus's spine and an angle of rotation of the fetus between a line connecting a central point of the fetus's torso with the reference point and a line connecting the central point thereof with the fetus's spine.

2. The method of claim 1, wherein the determining of the direction of the fetus's head comprises:
displaying a user interface for guiding scanning of the pregnant woman's body in the first direction;
displaying, based on the fetus's head not being detected in the first ultrasound image, a user interface for guiding rescanning of the pregnant woman's body; and
determining the direction of the fetus's head based on the fetus's head being detected in the first ultrasound image, and wherein the determining of the direction of the fetus's spine comprises:
displaying a user interface for guiding scanning of the pregnant woman's body in the second direction;
displaying a user interface for guiding rescanning of the pregnant woman's body based on the fetus's spine not being detected in the second ultrasound image; and
determining the direction of the fetus's spine based on the fetus's spine being detected in the second ultrasound image.

3. The method of claim 1, wherein the determining of the direction of the fetus's head comprises:
displaying a user interface for guiding scanning of the pregnant woman's body in the first direction;
determining the direction of the fetus's head based on the fetus's head being detected in the first ultrasound image; and
determining, based on the fetus's head not being detected in the first ultrasound image, the direction of the fetus's head based on a user input with respect to the first ultrasound image, and
wherein the determining of the direction of the fetus's spine comprises:
displaying a user interface for guiding scanning of the pregnant woman's body in the second direction;
determining the direction of the fetus's spine based on the fetus's spine being detected in the second ultrasound image; and
determining, based on the fetus's spine not being detected in the second ultrasound image, the direction of the fetus's spine based on a user input with respect to the second ultrasound image.

4. The method of claim 1, wherein the determining of the direction of the fetus's head comprises:
detecting the fetus's head in the first ultrasound image;
determining whether the fetus's head in the first ultrasound image is located right or left with respect to the torso of the fetus; and
displaying the fetus's head and the direction of the fetus's head on the first ultrasound image.

5. The method of claim 1, wherein the ultrasound image is an ultrasound image obtained by scanning the pregnant woman's body in the second direction, and
wherein the image representing the orientation of the fetus comprises at least one of an image having indicated thereon at least one of left and right sides of the fetus in the ultrasound image, an image showing a cross-section and the left and right sides of the fetus in the ultrasound image, and a mimic image showing the fetus three-dimensionally based on the orientation of the fetus.

6. The method of claim 1, wherein the image representing the orientation of the fetus comprises a mimic image showing the fetus three-dimensionally based on the orientation of the fetus, and
wherein the mimic image is rotated based on a user input.

7. The method of claim 1, wherein the image representing the orientation of the fetus comprises a mimic image showing the fetus three-dimensionally based on the orientation of the fetus, and
wherein the displaying of the image representing the orientation of the fetus comprises:
determining a posture of the fetus based on a leg of the fetus detected in the first ultrasound image; and
generating the mimic image based on the orientation and posture of the fetus and displaying the mimic image.

8. An apparatus for displaying an ultrasound image, the apparatus comprising:
at least one processor configured to:
determine a direction of a fetus's head based on a first ultrasound image obtained by scanning a pregnant woman's body in a first direction,
determine a direction of the fetus's spine based on a second ultrasound image obtained by scanning the pregnant woman's body in a second direction, and
determine an orientation of the fetus within the pregnant woman's body based on the directions of the fetus's head and the fetus's spine, wherein the orientation of the fetus is an orientation of an axis of the fetus relative to the pregnant woman's body; and
a display configured to display an image representing the orientation of the fetus together with an ultrasound image obtained by scanning the pregnant woman's body,
wherein the image representing the orientation of the fetus is displayed together with the ultrasound image obtained by scanning the pregnant woman's body without a mark indicating the direction of the fetus, and
wherein the display is further configured to display on a screen a display marker indicating an orientation of a probe for scanning the pregnant woman's body to obtain the ultrasound image,
wherein a probe marker is attached to one surface of the probe,
wherein the at least one processor is further configured to determine the orientation of the fetus based on the direction of the fetus's head, the direction of the fetus's spine, and the orientation of the probe, and scan the pregnant woman's body based on a position of the probe marker and a position of the display marker with respect to the first ultrasound image on the screen,
wherein the at least one processor is further configured to determine whether the fetus's head in the first ultrasound image is located right or left with respect to the fetus's torso, and if the fetus's head detected in the first ultrasound image is oriented in a right direction, the at least one processor determines the orientation of the fetus as corresponding to a vertex presentation of the fetus in the pregnant woman's body, and if the fetus's head detected in the first ultrasound image is oriented in a left direction, the at least one processor determines the orientation of the fetus as corresponding to a breech presentation of the fetus in the pregnant woman's body, wherein the display is further configured to display the fetus's spine and an angle of rotation of the fetus between a line connecting a central point of the fetus's torso with a reference point and a line connecting the central point thereof with the fetus's spine, wherein the at least one processor is further configured to detect the fetus's spine and the torso of the fetus in the second ultrasound image, and determine, based on the fetus's spine and the fetus's torso, an angle of rotation of the axis of the fetus with respect to the reference point, and wherein the display is further configured to display the fetus's spine and the angle of rotation on the second ultrasound image, determining the fetus's spine and the angle of rotation of the fetus between the line connecting the central point of the fetus's torso with the reference point and the line connecting the central point of the fetus's torso with the reference point and the line connecting the central point thereof with the fetus's spine.

9. The apparatus of claim 8, wherein the at least one processor is further configured to:

control the display to display a user interface for guiding scanning of the pregnant woman's body in the first direction, control the display to display, based on the fetus's head not being detected in the first ultrasound image, a user interface for guiding rescanning of the pregnant woman's body, determine the direction of the fetus's head based on the fetus's head being detected in the first ultrasound image, control the display to display a user interface for guiding scanning of the pregnant woman's body in the second direction, control the display to display, based on the fetus's spine not being detected in the second ultrasound image, a user interface for guiding rescanning of the pregnant woman's body, and determine the direction of the fetus's spine based on the fetus's spine being detected in the second ultrasound image.

10. The apparatus of claim 8, further comprising an input interface configured to receive a user input, wherein the at least one processor is further configured to:

control the display to display a user interface for guiding scanning of the pregnant woman's body in the first direction, determine the direction of the fetus's head based on the fetus's head being detected in the first ultrasound image, determine, based on the fetus's head not being detected in the first ultrasound image, the direction of the fetus's head based on a user input with respect to the first ultrasound image, control the display to display a user interface for guiding scanning of the pregnant woman's body in the second direction, determine the direction of the fetus's spine based on the fetus's spine being detected in the second ultrasound image, and determine, based on the fetus's spine not being detected in the second ultrasound image, the direction of the fetus's spine based on a user input with respect to the second ultrasound image.

11. The apparatus of claim 8, wherein the at least one processor is further configured to:

detect the fetus's head in the first ultrasound image, and determine whether the fetus's head in the first ultrasound image is located right or left with respect to the torso of the fetus, and wherein the display is further configured to display the fetus's head and the direction of the fetus's head on the first ultrasound image.

12. The apparatus of claim 8, wherein the ultrasound image is an ultrasound image obtained by scanning the pregnant woman's body in the second direction, and wherein the image representing the orientation of the fetus comprises at least one of an image having indicated thereon at least one of left and right sides of the fetus in the ultrasound image, an image showing a cross-section and the left and right sides of the fetus, in the ultrasound image, and a mimic image showing the fetus three-dimensionally based on the orientation of the fetus.

13. The apparatus of claim 8, further comprising an input interface configured to receive a user input, wherein the image representing the orientation of the fetus comprises a mimic image showing the fetus three-dimensionally based on the orientation of the fetus, and wherein the at least one processor is further configured to control the display to rotate the mimic image based on a user input.

14. The apparatus of claim 8, wherein the image representing the orientation of the fetus comprises a mimic image showing the fetus three-dimensionally based on the orientation of the fetus, and wherein the at least one processor is further configured to:

determine a posture of the fetus based on a leg of the fetus detected in the first ultrasound image, and generate the mimic image based on the orientation and posture of the fetus.

15. A non-transitory computer-readable recording medium having stored therein a program for performing the method of claim 1.

16. The method of claim 1, wherein the display marker is disposed at a predetermined position on the screen.

17. The apparatus of claim 8, wherein the display marker is disposed at a predetermined position on the screen.

* * * * *